US007319139B2

(12) United States Patent
Braslawsky et al.

(10) Patent No.: US 7,319,139 B2
(45) Date of Patent: Jan. 15, 2008

(54) TAG-72 SPECIFIC $C_H2$ DOMAIN DELETED ANTIBODIES

(75) Inventors: Gary R Braslawsky, San Diego, CA (US); Nabil Hanna, Rancho Santa Fe, CA (US); Paul Chinn, Carlsbad, CA (US); Kandasamy Hariharan, San Diego, CA (US)

(73) Assignee: Biogen Idec, Inc., Cambridge, MA (US)

( * ) Notice: Subject to any disclaimer, the term of this patent is extended or adjusted under 35 U.S.C. 154(b) by 0 days.

(21) Appl. No.: 10/058,069

(22) Filed: Jan. 29, 2002

(65) Prior Publication Data

US 2007/0280881 A1    Dec. 6, 2007

Related U.S. Application Data

(60) Provisional application No. 60/341,858, filed on Dec. 21, 2001, provisional application No. 60/331,481, filed on Nov. 16, 2001, provisional application No. 60/264,318, filed on Jan. 29, 2001.

(51) Int. Cl.
*C12P 21/08* (2006.01)
*C07K 16/00* (2006.01)
*A61K 39/395* (2006.01)
*C12P 21/04* (2006.01)
*C12N 5/06* (2006.01)

(52) U.S. Cl. .................... 530/387.3; 530/388.1; 530/388.8; 530/388.85; 530/391.7; 424/133.1; 424/141.1; 424/155.1; 424/181.1; 424/183.1; 435/69.6; 435/328; 435/330

(58) Field of Classification Search ............ 424/130.1, 424/133.1, 135.1, 136.1, 143.1, 155.1, 156.1, 424/181.1, 183.1; 530/391.3, 391.7, 387.1, 530/387.3, 387.7, 388.8
See application file for complete search history.

(56) References Cited

U.S. PATENT DOCUMENTS

| | | | |
|---|---|---|---|
| 5,435,990 A | 7/1995 | Cheng et al. | 424/153 |
| 5,512,443 A | 4/1996 | Schlom et al. | 435/7.23 |
| 5,756,065 A | 5/1998 | Wilson et al. | 424/1.53 |
| 5,877,291 A | 3/1999 | Mezes et al. | 530/387.3 |
| 5,891,996 A | 4/1999 | Mateo de Acosta del Rio et al. | 530/387.3 |
| 5,892,019 A | 4/1999 | Schlom et al. | 536/23.53 |
| 5,892,020 A | 4/1999 | Mezes et al. | 536/23.53 |
| 5,976,531 A | 11/1999 | Mezes et al. | 424/133.1 |
| 5,993,813 A | 11/1999 | Mezes et al. | 424/133.1 |
| 6,051,225 A | 4/2000 | Mezes et al. | 424/133.1 |
| 6,060,273 A | 5/2000 | Dirks et al. | |
| 6,103,889 A | 8/2000 | Whitlow et al. | 536/23.53 |
| 6,121,022 A | 9/2000 | Presta et al. | 435/69.7 |
| 6,165,745 A | 12/2000 | Ward et al. | 435/69.1 |
| 6,342,219 B1 * | 1/2002 | Thorpe et al. | |
| 6,348,581 B1 * | 2/2002 | Anderson et al. | |
| 6,897,044 B1 * | 5/2005 | Braslawsky et al. | |

FOREIGN PATENT DOCUMENTS

| | | |
|---|---|---|
| EP | 0 365 997 B1 | 9/1994 |
| EP | 0 327 378 B1 | 11/1996 |
| EP | 0 394 277 B1 | 1/1998 |
| WO | WO 89/01783 | 2/1989 |
| WO | WO 9413806 A1 * | 6/1994 |
| WO | WO 95 09917 | 4/1995 |
| WO | WO 97/11370 | 3/1997 |
| WO | WO 98 05787 | 2/1998 |
| WO | WO 98/11241 | 3/1998 |
| WO | WO 99 36105 | 7/1999 |
| WO | WO 99/43816 | 9/1999 |
| WO | WO 00/26394 | 5/2000 |
| WO | WO 200026394 A1 * | 5/2000 |

OTHER PUBLICATIONS

Rudikoff et al. Proc. Natl. Acad. Sci. USA 1982 vol. 79: p. 1979-1983.*
Goel et al. Journal of Biochemistry, 127:829-836, May 2000.*
Pavlinkova et al. The Journal of Nuclear Medicine, 40(9):1536-1546, Sep. 1999.*
Pavlinkova et al. Clinical Cancer Research, 5:2613-2619, Sep. 1999.*
Slavin-Chiorini et al. International Journal of Cancer, 53:97-103, 1993.*
Fundamental Immunology. 242, William E. Paul, M.D. ed., 3rd ed. 1993.*
Gillies et al. Human Antibodies and Hybridomas, 1(1):47-54, 1990.*
Beresford et al. International Journal of Cancer, 81(6):911-917, Jun. 11, 1999.*
Tankersley D. L. Immunological Reviews, 139:159-172, 1994.*
Kleinveld H. A. et al. Scandinavian Journal of Rheumatology Supplement, Suppl. 75 :157-163, 1988.*
Goel et al., Genetically engineered tetravalent single-chain Fv of the pancarcinoma monoclonal antibody CC49: improved biodistribution and potential for therapeutic application, (2000), *Cancer Research*, 60:6964-6971.
Jiang et al., Enhanced effector functions of dimeric forms of IDEC—C2B8 (Rituximab), 1999, *Blood*, 94(10):86A (Abstract).
Slavin-Chiorini et al., A CDR-grafted (humanized) domain-deleted antitumor antibody, (1997), *Cancer Biotherapy and Radiopharmaceuticals*, 5(12):305-316.

(Continued)

*Primary Examiner*—David J. Blanchard
(74) *Attorney, Agent, or Firm*—Pillsbury Winthrop Shaw Pittman LLP

(57) ABSTRACT

Methods, compositions and kits comprising dimeric antibodies for the treatment of neoplastic, autoimmune or other disorders are provided. The dimeric antibodies of the instant invention may comprise two antibody molecules ($H_4L_4$) having the same antigen binding specificity (homodimers) or, alternatively, may comprise two different antibody molecules having binding specificity for two distinct antigens (heterodimers). In preferred embodiments the antibody molecules comprising the dimers are non-covalently associated.

22 Claims, 13 Drawing Sheets

OTHER PUBLICATIONS

Slavin-Chiorini et al., Biological properties of chimeric domain-deleted anticarcinoma immunoglobulins, (1995), *Cancer Research*, 55:5957-5967.

Coloma et al., Design and production of novel tetravalent bispecific antibodies, (1997), *Nature Biotechnology*, 15(2):159-163.

Ghetie et al., Homodimerization of tumor-reactive monoclonal antibodies markedly increases their ability to induce growth arrest or apoptosis of tumor cells, (1997), *PNAS of USA*, 94:7509-7514.

International Search Report dated Apr. 11, 2003, for PCT Application PCT/US02/02373.

Mieike et al., (Jun. 22, 2000) Stabllized, long-term expression of heterodimeric proteins from tricistronic mRNA, *GENE, An International Journal on Genes, Genomes and Evoluation*, Elsevier (Darmstadt, DE), p. 108.

Kolb et al., (1997) Expression of a recombinant Monoclonal Antibody from a Bicistronic mRNA, *HYBRIDOMA*, Mary Ann Libert, Inc., vol. 16 (No. 5), pp. 421-426.

Lo et al., (1998) Expression and secretion of an assembled tetrameric CH2-deleted antibody in *E. coli*, *Human Antibodies and Hybridomas*, ELSEVIER Science B.V. (Amsterdam) vol. 3 (No. 3), pp. 123-128—ABSTRACT.

Fussenegger et al (1997), Autoregulated Multicistronic Expression Vectors provide One-step Cloning of Regulated Product Gene Expression in Mammalian Cells, *Biotechnol. Prog.*, American Chemical Society and American Institute of Chemical Engineers, pp. 733-740.

European Search Report, (Supplemental) Mar. 16, 2006, EP 02 80 2572.

* cited by examiner

Amino Acid Sequence of the C2B8 Heavy Chain

MGWSLILLFLVAVATRVLSQVQLQQPGAELVKPGASVKMSCKASGYTFTSYNM
HWVKQTPGRGLEWIGAIYPGNGDTSYNQKFKGKATLTADKSSSTAYMQLSSLTS
EDSAVYYCARSTYYGGDWYFNVWGAGTTVTVSAASTKGPSVFPLAPSSKSTSG
GTAALGCLVKDYFPEPVTVSWNSGALTSGVHTFPAVLQSSGLYSLSSVVTVPSSS
LGTQTYICNVNHKPSNTKVDKKAEPKSCDKTHTCPPCPAPELLGGPSVFLFPPKP
KDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSK
LTVDKSRWQQGNVFSCSVMHEALHNHYTQKSLSLSPGK*

Fig. 1A

Amino Acid Sequence of the C2B8 Domain Deleted Heavy Chain

MGWSLILLFLVAVATRVLSQVQLQQPGAELVKPGASVKMSCKASGYTFTSYNM
HWVKQTPGRGLEWIGAIYPGNGDTSYNQKFKGKATLTADKSSSTAYMQLSSLTS
EDSAVYYCARSTYYGGDWYFNVWGAGTTVTVSAASTKGPSVFPLAPSSKSTSG
GTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPGQPREPQVYTLPPSRDE
LTKNQVSLTCLVKGFYPSDIAVEWESNGQPENNYKTTPPVLDSDGSFFLYSKLTV
DKSRWQQGNVFSCSVMHEALHNHYTQKSI SLSPGK*

Fig. 1B

Nucleotide Sequence of the C2B8 Heavy Chain

ATGGGTTGGAGCCTCATCTTGCTCTTCCTTGTCGCTGTTGCTACGCGTGTCCTGTCCC
AGGTACAACTGCAGCAGCCTGGGGCTGAGCTGGTGAAGCCTGGGGCCTCAGTGAAG
ATGTCCTGCAAGGCTTCTGGCTACACATTTACCAGTTACAATATGCACTGGGTAAAA
CAGACACCTGGTCGGGGCCTGGAATGGATTGGAGCTATTTATCCCGGAAATGGTGAT
ACTTCCTACAATCAGAAGTTCAAAGGCAAGGCCACATTGACTGCAGACAAATCCTCC
AGCACAGCCTACATGCAGCTCAGCAGCCTGACATCTGAGGACTCTGCGGTCTATTAC
TGTGCAAGATCGACTTACTACGGCGGTGACTGGTACTTCAATGTCTGGGGCGCAGGG
ACCACGGTCACCGTCTCTGCAGCTAGCACCAAGGGCCCATCGGTCTTCCCCCTGGCA
CCCTCCTCCAAGAGCACCTCTGGGGGCACAGCGGCCCTGGGCTGCCTGGTCAAGGAC
TACTTCCCCGAACCGGTGACGGTGTCGTGGAACTCAGGCGCCCTGACCAGCGGCGTG
CACACCTTCCCGGCTGTCCTACAGTCCTCAGGACTCTACTCCCTCAGCAGCGTGGTGA
CCGTGCCCTCCAGCAGCTTGGGCACCCAGACCTACATCTGCAACGTGAATCACAAGC
CCAGCAACACCAAGGTGGACAAGAAAGCAGAGCCCAAATCTTGTGACAAAACTCAC
ACATGCCCACCGTGCCCAGCACCTGAACTCCTGGGGGGACCGTCAGTCTTCCTCTTCC
CCCCAAAACCCAAGGACACCCTCATGATCTCCCGGACCCCTGAGGTCACATGCGTGG
TGGTGGACGTGAGCCACGAAGACCCTGAGGTCAAGTTCAACTGGTACGTGGACGGC
GTGGAGGTGCATAATGCCAAGACAAAGCCGCGGGAGGAGCAGTACAACAGCACGTA
CCGTGTGGTCAGCGTCCTCACCGTCCTGCACCAGGACTGGCTGAATGGCAAGGAGTA
CAAGTGCAAGGTCTCCAACAAAGCCCTCCCAGCCCCCATCGAGAAAACCATCTCCAA
AGCCAAAGGGCAGCCCCGAGAACCACAGGTGTACACCCTGCCCCCATCCCGGGATG
AGCTGACCAAGAACCAGGTCAGCCTGACCTGCCTGGTCAAAGGCTTCTATCCCAGCG
ACATCGCCGTGGAGTGGGAGAGCAATGGGCAGCCGGAGAACAACTACAAGACCACG
CCTCCCGTGCTGGACTCCGACGGCTCCTTCTTCCTCTACAGCAAGCTCACCGTGGACA
AGAGCAGGTGGCAGCAGGGGAACGTCTTCTCATGCTCCGTGATGCATGAGGCTCTGC
ACAACCACTACACGCAGAAGAGCCTCTCCCTGTCTCCGGGTAAATGA

Fig. 2A

Nucleotide Sequence of the C2B8 Domain Deleted Heavy Chain

ATGGGTTGGAGCCTCATCTTGCTCTTCCTTGTCGCTGTTGCTACGCGTGTCCTGTCCC
AGGTACAACTGCAGCAGCCTGGGGCTGAGCTGGTGAAGCCTGGGGCCTCAGTGAAG
ATGTCCTGCAAGGCTTCTGGCTACACATTTACCAGTTACAATATGCACTGGGTAAAA
CAGACACCTGGTCGGGGCCTGGAATGGATTGGAGCTATTTATCCCGGAAATGGTGAT
ACTTCCTACAATCAGAAGTTCAAAGGCAAGGCCACATTGACTGCAGACAAATCCTCC
AGCACAGCCTACATGCAGCTCAGCAGCCTGACATCTGAGGACTCTGCGGTCTATTAC
TGTGCAAGATCGACTTACTACGGCGGTGACTGGTACTTCAATGTCTGGGGCGCAGGG
ACCACGGTCACCGTCTCTGCAGCTAGCACCAAGGGCCCATCGGTCTTCCCCCTGGCA
CCCTCCTCCAAGAGCACCTCTGGGGGCACAGCGGCCCTGGGCTGCCTGGTCAAGGAC
TACTTCCCCGAACCGGTGACGGTGTCGTGGAACTCAGGCGCCCTGACCAGCGGCGTG
CACACCTTCCCGGCTGTCCTACAGTCCTCAGGACTCTACTCCCTCAGCAGCGTGGTGA
CCGTGCCCTCCAGCAGCTTGGGCACCCAGACCTACATCTGCAACGTGAATCACAAGC
CCAGCAACACCAAGGTGGACAAGAAAGTTGAGCCCAAATCTTGTGACAAAACTCAC
ACATGCCCACCGTGCCCAGGGCAGCCCCGAGAACCACAGGTGTACACCCTGCCCCCA
TCCCGGGATGAGCTGACCAAGAACCAGGTCAGCCTGACCTGCCTGGTCAAAGGCTTC
TATCCCAGCGACATCGCCGTGGAGTGGGAGAGCAATGGGCAGCCGGAGAACAACTA
CAAGACCACGCCTCCCGTGCTGGACTCCGACGGCTCCTTCTTCCTCTACAGCAAGCTC
ACCGTGGACAAGAGCAGGTGGCAGCAGGGGAACGTCTTCTCATGCTCCGTGATGCAT
GAGGCTCTGCACAACCACTACACGCAGAAGAGCCTCTCCCTGTCTCCGGGTAAATGA

Fig. 2B

Nucleotide Sequence of the C2B8 Light Chain

ATGGATTTTCAGGTGCAGATTATCAGCTTCCTGCTAATCAGTGCTTCAGTCAT
AATGTCCAGAGGACAAATTGTTCTCTCCCAGTCTCCAGCAATCCTGTCTGCAT
CTCCAGGGGAGAAGGTCACAATGACTTGCAGGGCCAGCTCAAGTGTAAGTTA
CATCCACTGGTTCCAGCAGAAGCCAGGATCCTCCCCCAAACCCTGGATTTAT
GCCACATCCAACCTGGCTTCTGGAGTCCCTGTTCGCTTCAGTGGCAGTGGGTC
TGGGACTTCTTACTCTCTCACAATCAGCAGAGTGGAGGCTGAAGATGCTGCC
ACTTATTACTGCCAGCAGTGGACTAGTAACCCACCCACGTTCGGAGGGGGGA
CCAAGCTGGAAATCAAACGTACGGTGGCTGCACCATCTGTCTTCATCTTCCCG
CCATCTGATGAGCAGTTGAAATCTGGAACTGCCTCTGTTGTGTGCCTGCTGAA
TAACTTCTATCCCAGAGAGGCCAAAGTACAGTGGAAGGTGGATAACGCCCTC
CAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAA
CACAAAGTCTACGCCTGCGAAGTCACCCATCAGGGCCTGAGCTCGCCCGTCA
CAAAGAGCTTCAACAGGGGAGAGTGTTGA

Fig. 3A

Amino Acid Sequence of the C2B8 Light Chain

MDFQVQIISFLLISASVIMSRGQIVLSQSPAILSASPGEKVTMTCRASSSVSYIHWF
QQKPGSSPKPWIYATSNLASGVPVRFSGSGSGTSYSLTISRVEAEDAATYYCQQW
TSNPPTFGGGTKLEIKRTVAAPSVFIFPPSDEQLKSGTASVVCLLNNFYPREAKVQ
WKVDNALQSGNSQESVTEQDSKDSTYSLSSTLTLSKADYEKHKVYACEVTHQG
LSSPVTKSFNRGEC*

Fig. 3B

Amino Acid Sequence of the HuCC49 Domain Deleted Heavy Chain

MGWSLILLFLVAVATRVLSQVQLVQSGAEVVKPGASVKISCKASGYTFTDHAIH
WVKQNPGQRLEWIGYFSPGNDDFKYNERFKGKATLTADTSASTAYVELSSLRSE
DTAVYFCTRSLNMAYWGQGTLVTVSSASTKGPSVFPLAPSSKSTSGGTAALGCL
VKDYFPEPVTVSWNSGALTSGVHTFPAVLQSSGLYSLSSVVTVPSSSLGTQTYIC
NVNHKPSNTKVDKKVEPKSCDKTHTCPPCPGQPREPQVYTLPPSRDELTKNQVS
LTCLVKGFYPSDIAVEWESNGQPENNYKTTPPVLDSDGSFFLYSKLTVDKSRWQ
QGNVFSCSVMHEALHNHYTQKSLSLSPGK*

Fig. 4A

Nucleotide Sequence of the HuCC49 Domain Deleted Heavy Chain

ATGGGTTGGAGCCTCATCTTGCTCTTCCTTGTCGCTGTTGCTACGCGTGTCCTG
TCCCAGGTCCAGCTGGTGCAGTCCGGCGCTGAGGTGGTGAAACCTGGGGCTT
CCGTGAAGATTTCCTGCAAGGCAAGCGGCTACACCTTCACTGATCACGCAAT
CCACTGGGTGAAACAGAATCCTGGACAGCGCCTGGAGTGGATTGGATATTTC
TCTCCCGGAAACGATGATTTTAAGTACAATGAGAGGTTCAAGGGCAAGGCCA
CACTGACTGCAGACACATCTGCCAGCACTGCCTACGTGGAGCTCTCCAGCCT
GAGATCCGAGGATACTGCAGTGTACTTCTGCACAAGATCCCTGAATATGGCC
TACTGGGGACAGGGAACCCTGGTCACCGTCTCCAGCGCTAGCACCAAGGGCC
CATCGGTCTTCCCCCTGGCACCCTCCTCCAAGAGCACCTCTGGGGGCACAGC
GGCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTAC
AGTCCTCAGGACTCTACTCCCTCAGCAGCGTGGTGACCGTGCCCTCCAGCAG
CTTGGGCACCCAGACCTACATCTGCAACGTGAATCACAAGCCCAGCAACACC
AAGGTGGACAAGAAAGTTGAGCCCAAATCTTGTGACAAAACTCACACATGCC
CACCGTGCCCAGGGCAGCCCCGAGAACCACAGGTGTACACCCTGCCCCCATC
CCGGGATGAGCTGACCAAGAACCAGGTCAGCCTGACCTGCCTGGTCAAAGGC
TTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTC
TACAGCAAGCTCACCGTGGACAAGAGCAGGTGGCAGCAGGGGAACGTCTTCT
CATGCTCCGTGATGCATGAGGCTCTGCACAACCACTACACGCAGAAGAGCCT
CTCCCTGTCTCCGGGTAAATGA

Fig. 4B

Amino Acid Sequence of the HuCC49 Light Chain

MDSQAQVLMLLLLWVSGTCGDIVMSQSPDSLAVSLGERVTLNCKSSQSLLYSGN
QKNYLAWYQQKPGQSPKLLIYWASARESGVPDRFSGSGSGTDFTLTISSVQAED
VAVYYCQQYYSYPLTFGAGTKLELKRTVAAPSVFIFPPSDEQLKSGTASVVCLLN
NFYPREAKVQWKVDNALQSGNSQESVTEQDSKDSTYSLSSTLTLSKADYEKHK
VYACEVTHQGLSSPVTKSFNRGEC*

Fig. 5A

Nucleotide Sequence of the HuCC49 Light Chain

ATGGATAGCCAGGCCCAGGTGCTCATGCTCCTGCTGCTGTGGGTGAGCGGCA
CATGCGGCGACATCGTGATGAGCCAGTCTCCAGACTCCCTGGCCGTGTCCCT
GGGCGAGAGGGTGACTCTGAATTGCAAGTCCAGCCAGTCCCTGCTCTATAGC
GGAAATCAGAAGAACTATCTCGCCTGGTATCAGCAGAAACCAGGGCAGAGC
CCTAAACTGCTGATTTACTGGGCATCCGCTAGGGAATCCGGCGTGCCTGATCG
CTTCAGCGGCAGCGGATCTGGGACAGACTTCACTCTGACAATCAGCAGCGTG
CAGGCAGAAGACGTGGCAGTCTATTATTGTCAGCAGTATTATAGCTATCCCCT
CACATTCGGCGCTGGCACCAAGCTGGAACTGAAACGTACGGTGGCTGCACCA
TCTGTCTTCATCTTCCCGCCATCTGATGAGCAGTTGAAATCTGGAACTGCCTC
TGTTGTGTGCCTGCTGAATAACTTCTATCCCAGAGAGGCCAAAGTACAGTGG
AAGGTGGATAACGCCCTCCAATCGGGTAACTCCCAGGAGAGTGTCACAGAGC
AGGACAGCAAGGACAGCACCTACAGCCTCAGCAGCACCCTGACGCTGAGCA
AAGCAGACTACGAGAAACACAAAGTCTACGCCTGCGAAGTCACCCATCAGG
GCCTGAGCTCGCCCGTCACAAAGAGCTTCAACAGGGGAGAGTGTTGA

Fig. 5B

Amino Acid Sequence of C5E10 Heavy Chain

MAVLALLFCLVTFPSCILSQVQLKESGPGLVAPSQSLSITCTVSGFSLTDYGVNWV
RQPPGKGLEWLGMIWDNGRTDYNSALKSRLSINKDNSKSQVFLKMTSLQTDDTA
RYYCARCYYGSSPYFDYWGQGTTLTVSSASTKGPSVFPLAPSSKSTSGGTAALGC
LVKDYFPEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDTLMISRT
PEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQ
GNVFSCSVMHEALHNHYTQKSLSLSPGK

Fig. 6A

Amino Acid Sequence of C5E10 Domain Deleted Heavy Chain

MAVLALLFCLVTFPSCILSQVQLKESGPGLVAPSQSLSITCTVSGFSLTDYGVNWV
RQPPGKGLEWLGMIWDNGRTDYNSALKSRLSINKDNSKSQVFLKMTSLQTDDTA
RYYCARCYYGSSPYFDYWGQGTTLTVSSASTKGPSVFPLAPSSKSTSGGTAALGC
LVKDYFPEPVTVSWNSGALTSGVHTFPAVLQSSGLYSLSSVVTVPSSSLGTQTYIC
NVNHKPSNTKVDKKVEPKSCDKTHTCPPCPGQPREPQVYTLPPSRDELTKNQVSL
TCLVKGFYPSDIAVEWESNGQPENNYKTTPPVLDSDGSFFLYSKLTVDKSRWQQ
GNVFSCSVMHEALHNHYTQKSLSLSPGK

Fig. 6B

Nucleotide Sequence of C5E10 Heavy Chain

ATGGCTGTCTTAGCGCTACTCTTCTGCCTGGTAACATTCCCAAGCTGTATCCTTTCCC
AGGTGCAGCTGAAGGAGTCAGGACCTGGCCTGGTGGCGCCCTCACAGAGCCTGTCCA
TCACATGCACCGTCTCAGGGTTCTCATTAACCGACTATGGTGTAAACTGGGTTCGCCA
GCCTCCAGGAAAGGGTCTGGAGTGGCTTGGAATGATATGGGATAATGGAAGAACAG
ACTATAATTCAGCTCTCAAATCCAGACTGAGCATCAACAAGGACAACTCCAAGAGCC
AAGTTTTCTTAAAAATGACCAGTCTGCAAACTGATGACACAGCCAGGTACTACTGTG
CCAGATGCTATTACGGTAGTAGCCCTTACTTTGACTACTGGGGCCAAGGCACCACTC
TCACCGTCTCCTCAGCTAGCACCAAGGGCCCATCGGTCTTCCCCCTGGCACCCTCCTC
CAAGAGCACCTCTGGGGGCACAGCGGCCCTGGGCTGCCTGGTCAAGGACTACTTCCC
CGAACCGGTGACGGTGTCGTGGAACTCAGGCGCCCTGACCAGCGGCGTGCACACCTT
CCCGGCTGTCCTACAGTCCTCAGGACTCTACTCCCTCAGCAGCGTGGTGACCGTGCCC
TCCAGCAGCTTGGGCACCCAGACCTACATCTGCAACGTGAATCACAAGCCCAGCAAC
ACCAAGGTGGACAAGAAAGTTGAGCCCAAATCTTGTGACAAAACTCACACATGCCC
ACCGTGCCCAGCACCTGAACTCCTGGGGGGACCGTCAGTCTTCCTCTTCCCCCCAAA
ACCCAAGGACACCCTCATGATCTCCCGGACCCCTGAGGTCACATGCGTGGTGGTGGA
CGTGAGCCACGAAGACCCTGAGGTCAAGTTCAACTGGTACGTGGACGGCGTGGAGG
TGCATAATGCCAAGACAAAGCCGCGGGAGGAGCAGTACAACAGCACGTACCGTGTG
GTCAGCGTCCTCACCGTCCTGCACCAGGACTGGCTGAATGGCAAGGAGTACAAGTGC
AAGGTCTCCAACAAAGCCCTCCCAGCCCCCATCGAGAAAACCATCTCCAAAGCCAAA
GGGCAGCCCCGAGAACCACAGGTGTACACCCTGCCCCCATCCCGGGATGAGCTGACC
AAGAACCAGGTCAGCCTGACCTGCCTGGTCAAAGGCTTCTATCCCAGCGACATCGCC
GTGGAGTGGGAGAGCAATGGGCAGCCGGAGAACAACTACAAGACCACGCCTCCCGT
GCTGGACTCCGACGGCTCCTTCTTCCTCTACAGCAAGCTCACCGTGGACAAGAGCAG
GTGGCAGCAGGGGAACGTCTTCTCATGCTCCGTGATGCATGAGGCTCTGCACAACCA
CTACACGCAGAAGAGCCTCTCCCTGTCTCCGGGTAAATGA

Fig. 7A

Nucleotide Sequence of C5E10 Domain Deleted Heavy Chain

ATGGCTGTCTTAGCGCTACTCTTCTGCCTGGTAACATTCCCAAGCTGTATCCTTTCCC
AGGTGCAGCTGAAGGAGTCAGGACCTGGCCTGGTGGCGCCCTCACAGAGCCTGTCCA
TCACATGCACCGTCTCAGGGTTCTCATTAACCGACTATGGTGTAAACTGGGTTCGCCA
GCCTCCAGGAAAGGGTCTGGAGTGGCTTGGAATGATATGGGATAATGGAAGAACAG
ACTATAATTCAGCTCTCAAATCCAGACTGAGCATCAACAAGGACAACTCCAAGAGCC
AAGTTTTCTTAAAAATGACCAGTCTGCAAACTGATGACACAGCCAGGTACTACTGTG
CCAGATGCTATTACGGTAGTAGCCCTTACTTTGACTACTGGGGCCAAGGCACCACTC
TCACCGTCTCCTCAGCTAGCACCAAGGGCCCATCGGTCTTCCCCCTGGCACCCTCCTC
CAAGAGCACCTCTGGGGGCACAGCGGCCCTGGGCTGCCTGGTCAAGGACTACTTCCC
CGAACCGGTGACGGTGTCGTGGAACTCAGGCGCCCTGACCAGCGGCGTGCACACCTT
CCCGGCTGTCCTACAGTCCTCAGGACTCTACTCCCTCAGCAGCGTGGTGACCGTGCCC
TCCAGCAGCTTGGGCACCCAGACCTACATCTGCAACGTGAATCACAAGCCCAGCAAC
ACCAAGGTGGACAAGAAAGTTGAGCCCAAATCTTGTGACAAAACTCACACATGCCC
ACCGTGCCCAGGGCAGCCCCGAGAACCACAGGTGTACACCCTGCCCCCATCCCGGGA
TGAGCTGACCAAGAACCAGGTCAGCCTGACCTGCCTGGTCAAAGGCTTCTATCCCAG
CGACATCGCCGTGGAGTGGGAGAGCAATGGGCAGCCGGAGAACAACTACAAGACCA
CGCCTCCCGTGCTGGACTCCGACGGCTCCTTCTTCCTCTACAGCAAGCTCACCGTGGA
CAAGAGCAGGTGGCAGCAGGGGAACGTCTTCTCATGCTCCGTGATGCATGAGGCTCT
GCACAACCACTACACGCAGAAGAGCCTCTCCCTGTCTCCGGGTAAATGA

Fig. 7B

Nucleotide Sequence of C5E10 Light Chain

ATGGGCATCAAGATGGAGTCACATTCTCTGGTCTTTGTATACATGTTGCTGTG
GTTGTCTGGTGTTGAAGGAGACATTGTGATGATCCAGTCTCACAAATTCATGT
CCACATCAGTAGGAGACAGGGTCAGCATCACCTGCAAGGCCAGTCAGGATGT
GGGTACTGCTGTCGCCTGGTATCAACAGAAACCAGGACAATCTCCTAAACTA
CTGATTTACTGGTCATCCACCCGGCACACTGGAGTCCCTGATCGCTTCACAGG
CAGTGGATCTGGGACAGATTTCACTCTCACCATTAGCAATGTGCAGTCTGAA
GACTTGGCAGATTATTTCTGTCAGTTATATAGCAGCTATCCTCTCACGTTCGG
AGGGGGGACCAAGCTGGAAATCAAACGTACGGTGGCTGCACCATCTGTCTTC
ATCTTCCCGCCATCTGATGAGCAGTTGAAATCTGGAACTGCCTCTGTTGTGTG
CCTGCTGAATAACTTCTATCCCAGAGAGGCCAAAGTACAGTGGAAGGTGGAT
AACGCCCTCCAATCGGGTAACTCCCAGGAGAGTGTCACAGAGCAGGACAGC
AAGGACAGCACCTACAGCCTCAGCAGCACCCTGACGCTGAGCAAAGCAGAC
TACGAGAAACACAAAGTCTACGCCTGCGAAGTCACCCATCAGGGCCTGAGCT
CGCCCGTCACAAAGAGCTTCAACAGGGGAGAGTGTTGA

Fig. 8A

Amino Acid Sequence of C5E10 Light Chain

MGIKMESHSLVFVYMLLWLSGVEGDIVMIQSHKFMSTSVGDRVSITCKASQDVG
TAVAWYQQKPGQSPKLLIYWSSTRHTGVPDRFTGSGSGTDFTLTISNVQSEDLAD
YFCQLYSSYPLTFGGGTKLEIKRTVAAPSVFIFPPSDEQLKSGTASVVCLLNNFYP
REAKVQWKVDNALQSGNSQESVTEQDSKDSTYSLSSTLTLSKADYEKHKVYAC
EVTHQGLSSPVTKSFNRGEC

Fig. 8B ated surface antigens (BR96 and HER-2). The Ghetie dimers also included antibodies to several human B-cell markers (CD20, CD19, CD21, CD22). In this approach, one portion of the molecule was functionalized using a linker designed to introduce a reactive thiol on the antibody, while the other Ab portion used a linker to introduce a maleimido group. When purified from unreacted linkers and mixed together, the two antibodies complex by formation of a thioether (non-reducible) bridge that links the two IgG molecules, and forming a 300 kDa, tetravalent antibody ($H_4L_4$) molecule.
TAG-72 SPECIFIC $C_H2$ DOMAIN DELETED ANTIBODIES

CROSS REFERENCE TO RELATED APPLICATIONS

Priority is claimed to U.S. Provisional Application No. 60/341,858 filed Dec. 21, 2001, U.S. Provisional Application No. 60/264,318 filed Jan. 29, 2001, and U.S. Provisional Application No. 60/331,481 filed Nov. 16, 2001 each of which is incorporated in its entirety herein by reference.

FIELD OF THE INVENTION

In a broad aspect the present invention generally relates to a novel process for the preparation of biologically active antibody dimers and pharmaceutically acceptable compositions containing such dimers. These dimers may comprise two antibody molecules ($H_4L_4$) having the same antigen binding specificity (homodimers) or, alternatively, may comprise two different antibody molecules having binding specificity for two distinct antigens (heterodimers). The subject antibody dimers demonstrate improved binding characteristics over their monomeric counterparts and are useful for inducing hyper-cross-linking of membrane antigens. The present invention further relates to the use of biologically active antibody dimers for the preferential killing or inhibition of selected cell populations in the treatment of diseases such as cancer and immune disorders.

BACKGROUND OF THE INVENTION

Monoclonal antibodies were once thought to be an ideal way to target malignant tissues, by delivering a killing agent, while leaving healthy tissue intact. However, their clinical potential is often limited due to the need to covalently couple the killing agent to the monoclonal antibody. Thus, in an effort to alleviate such limitations, bispecific antibodies were developed, which remain bivalent, but are specific for a target cell on one arm of the antibody and a killing agent on the other arm. The killing agent can be a toxin, a drug, a chelated radioisotope, or, more preferably, a cytotoxic effector cell.

Monoclonal antibodies can also show therapeutic activity against specific cells, e.g., malignant tissues based on the interaction of the Fc portion of the antibody heavy chain with other components of the immune system, such as the complement cascade or by binding to Fcγ receptors or various cytotoxic effector cell types.

Another means of effecting cell death comprises inducing the cross-linking of membrane antigens. Previous studies have indicated that antibody cross-linking of membrane B-cell markers (e.g., surface IgM, Valentine et al., *Eur. J. Immunol.* 22:3141 (1992); and MHC class II, Newell et al., *PNAS* 90:10459 (1993)) can inhibit malignant B cell proliferation and in many cases induce apoptosis (e.g., programmed cell death) in vitro.

Shan et al. (*Blood* 91:1644-1653) demonstrated that hyper-cross-linking of the CD20 antigen, by using the murine 1F5 antibody cross-linked with a goat anti-mouse IgG, inhibited growth of several human B-lymphoma cell lines in vitro. Similar results have now been published for both CD19 and CD22 when cross-linking of membrane bound MAb was amplified with a anti-mouse IgG (Chaouchi et al., *J. Immunol.* 154:3096 (1995)).

It may be possible that hyper cross-linking of these surface membrane markers could augment the existing anti-tumor activities of MAb's like C2B8, a chimeric monoclonal antibody specific for CD20, and increase therapeutic effectiveness. Therefore, molecules that can induce cell death in a pharmaceutically acceptable format would potentially provide an attractive therapeutic agent for immunotherapy of neoplastic disease.

Apparently with that goal in mind, Wolff et al. (*Cancer Res.* 53:2560-2565 (1993)) and Ghetie (*PNAS* 94:7509-7514 (1997)) have reported the chemical synthesis of several IgG/IgG homodimers to carcinoma associ However, unfortunately, the yields of the 300 kDa IgG-homodimer were very low (20-25%) and were similar or lower than the CD19 homodimer, which ranged from 20-30% (Ghetie et al., *PNAS* 94:7509-7514 (1997)). Reducing SDS-PAGE gels of purified homodimer showed only a small percentage was linked via a thioether bond, indicating most of the dimers formed using this methodology may have been naturally occurring or mediated through disulfide bridging. Nevertheless, all of the purified dimers were growth inhibitory, although only the anti-carcinoma (Her-2) dimer and not homodimers directed against B cell markers CD19, CD20, CD21, CD22 were reported to be apoptotic. Additionally, the anti-CD19 homodimer was tested in animal models and shown to have anti-tumor activity. However, there is a need in the art for a more efficient method for producing homodimers, in particular for homodimers or heterodimers that are capable of initiating apoptosis, e.g., in proliferating malignant B-cells populations.

Among the problems associated with bispecific or dimeric antibodies is the response generated by the human immune system itself, which may respond to the antibody as a foreign agent. For instance, patients treated with drugs or radionuclides complexed with murine monoclonal antibodies (which have been the most commonly used targeting antibodies for human) develop circulating human anti-mouse antibodies (HAMAs) and a generalized immediate type-III hypersensitivity reaction to the antibody moiety of the conjugate. This problem is compounded when such antibodies are chemically linked. Furthermore, even when adverse side effects are minimal (for example, as in a single administration), circulating HAMAs decrease the effective concentration of the targeting agent in the patient and therefore limiting the bispecific antibody from reaching the target site.

As such, it is an object of the present invention to provide low toxicity compounds that may be used to target neoplastic cells.

It is another object of the invention to provide compounds that may effectively used to treat immune disorders.

It is still another object of the present invention to provide dimeric antibodies having high binding affinities and low immunogenicity.

SUMMARY OF THE INVENTION

These and other objectives are provided for by the present invention which, in a broad sense, is directed to methods, kits, compounds and compositions that may be used in the treatment of neoplastic, immune or other disorders. To that end, the present invention provides for dimeric antibodies comprising four heavy and four light chains ($H_4L_4$) that may be used to treat patients suffering from a variety of disorders. In this respect, the dimeric antibodies or immunoglobulins of the present invention have been surprisingly found to exhibit biochemical characteristics that make them particularly useful for the treatment of patients. More specifically, it was unexpectedly found that selectively modified antibodies will associate non-covalently to form stable Ig/Ig dimers or tetravalent molecules having beneficial properties with regard to preferential killing or inhibition of selected cell populations. These dimeric constructs may be homodimers when two identical monomeric subunits are associated with each other or heterodimers when two different subunits are non-covalently associated. In any event, the dimeric constructs of the present invention may be used in an unconjugated form to effectively target and kill selected cell populations through mechanisms where increased binding or hyper cross-linking of membrane antigens are important for inducing biological activity. Conversely, due to their effective localization, the disclosed tetravalent constructs may be associated with cytotoxic agents such as radioisotopes to provide effective immunoconjugates having reduced toxicity.

Accordingly, one important aspect of the present invention comprises the use of the dimeric constructs of the present invention to treat a mammal for a disorder comprising administering a therapeutically effective amount of a dimeric antibody to said mammal. In this respect those skilled in the art will appreciate that the dimeric or tetravalent antibody maybe administered in its original state, unlinked to any other compound or it may be associated with a cytotoxic agent. In the case of the former, the dimeric antibodies may be used to induce apoptosis in the target cell population or effectively block cell surface receptors necessary for the growth of neoplastic cells. When linked to cytotoxic agents such as radioisotopes or drugs, the dimeric antibodies of the instant invention are particularly useful for the treatment or diagnosis of neoplastic disorders. That is, dimeric radioimmunoconjugates associated with a radioisotope such as $^{90}Y$ or $^{131}I$ may be administered to patients suffering from any one of a number of cancers. The surprising properties of the disclosed compounds (i.e. increased binding affinities and low immunogenicity) substantially reduces associated toxicity to healthy organs while delivering therapeutically effective doses directly to the tumor. Additionally, the tetravalent MAb forms disclosed herein tend to exhibit rapid blood clearance when compared to prior art chemically linked dimeric antibodies. This surprising property of the disclosed tetravalent antibodies will substantially reduce myelotoxicity when they are used in radioimmunotherapy while maintaining effective tumor localization. The reduction in myelotoxicity makes the present invention particularly useful in the treatment of patients that are myelosuppressed or otherwise myelocompromised.

As will be discussed in some detail below, the present invention further comprises kits comprising containers having the disclosed dimeric antibodies dispersed therein, compounds and compositions comprising the dimeric antibodies and methods of forming the dimeric antibodies. With respect to this latter aspect of the invention, it has been surprisingly found that the disclosed stable dimeric constructs form rapidly and spontaneously upon production of the monomeric subunits by the engineered host cells. That is, when the host cells produce monomeric subunits such as the modified antibodies set forth herein they rapidly form dimeric constructs through non-covalent associations. As discussed in more detail below, these non-covalent associations have been found to be surprisingly strong and provide for novel tetravalent heterodimers and homodimers that are particularly useful for the treatment of various disorders as described in the instant disclosure. This is in contrast to prior art dimeric constructs that employed covalent bonds typically requiring complicated production methodology and often leading to unwanted byproducts or immunogenicity.

Other objects, features and advantages of the present invention will be apparent to those skilled in the art from a consideration of the following detailed description of preferred exemplary embodiments thereof.

BRIEF DESCRIPTION OF THE FIGURES

FIGS. 1A and 1B show, respectively, an amino acid sequence of an intact $C2B_8$ heavy chain (SEQ ID NO: 1) and an amino acid sequence of a derived domain deleted $C2B_8$ construct (SEQ ID NO: 2) wherein the $C_H2$ domain has been deleted;

FIGS. 2A and 2B show, respectively, a nucleotide sequence of an intact $C2B_8$ heavy chain (SEQ ID NO: 3) and a nucleotide sequence of a derived domain deleted $C2B_8$ construct (SEQ ID NO: 4) wherein the $C_H2$ domain has been deleted;

FIGS. 3A and 3B show, respectively, a nucleotide sequence of a $C2B_8$ light chain (SEQ ID NO: 5) and the corresponding amino acid sequence (SEQ ID NO: 6) of the same light chain;

FIGS. 4A and 4B show, respectively the amino acid sequence of a huCC49 domain deleted heavy chain (SEQ ID NO: 7) wherein the $C_H2$ domain has been deleted and a corresponding nucleotide sequence (SEQ ID NO: 8) for the same heavy chain;

FIGS. 5A and 5B show, respectively, an amino acid sequence of a huCC49 light chain (SEQ ID NO: 9) and a corresponding nucleotide sequence (SEQ ID NO: 10) of the same light chain;

FIGS. 6A and 6B show, respectively, an amino acid sequence of an intact C5E10 heavy chain (SEQ ID NO: 11) and an amino acid sequence of a derived domain deleted C5E10 construct (SEQ ID NO: 12) wherein the $C_H2$ domain has been deleted;

FIGS. 7A and 7B show, respectively, a nucleotide sequence of an intact C5E10 heavy chain (SEQ ID NO: 13) and a nucleotide sequence of a derived domain deleted C5E10 construct (SEQ ID NO: 14) wherein the $C_H2$ domain has been deleted;

FIGS. 8A and 8B show, respectively, a nucleotide sequence of a C5E10 light chain (SEQ ID NO: 15) and the corresponding amino acid sequence (SEQ ID NO: 16) of the same light chain;

DETAILED DESCRIPTION OF THE INVENTION

Figure 9:
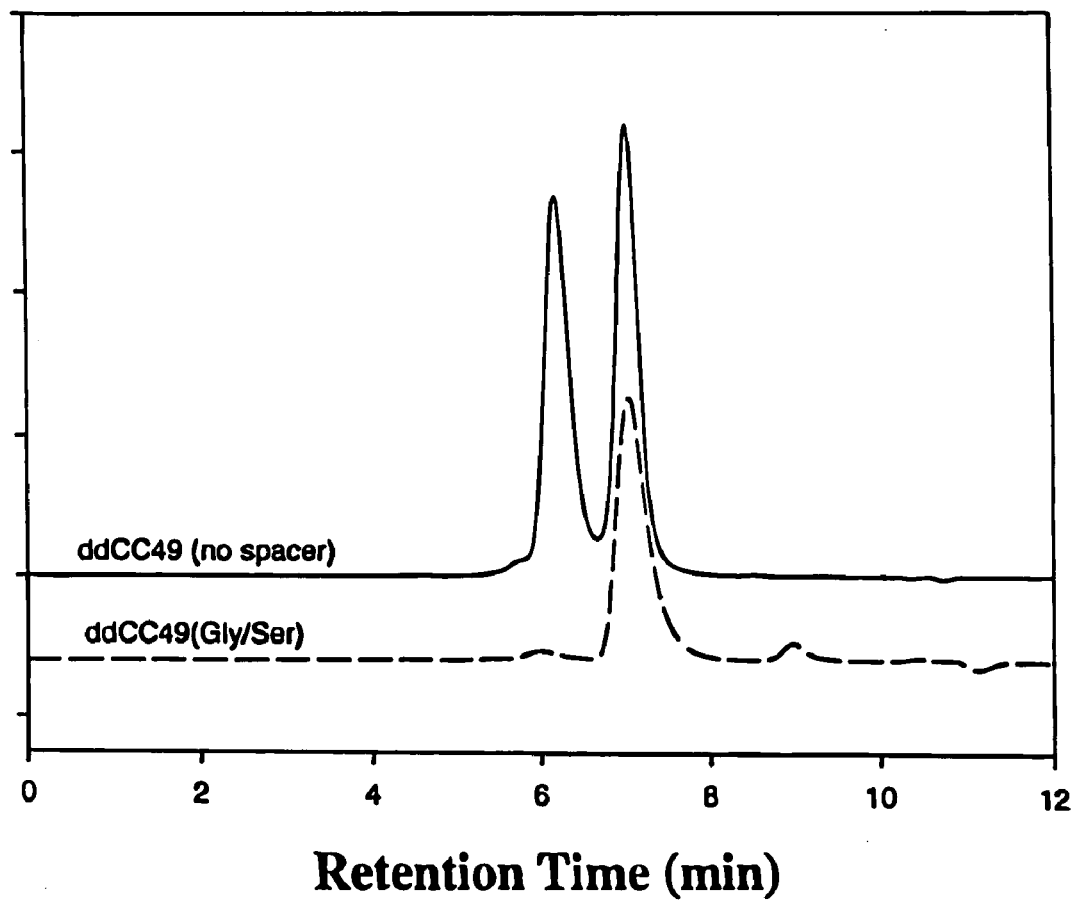
FIG. 9 is a graphical representation of a HPLC-SEC chromatograph of CC49.$\Delta C_H2$ showing the separate elution of the dimeric and monomeric variants of the antibody construct.
Figure 10:
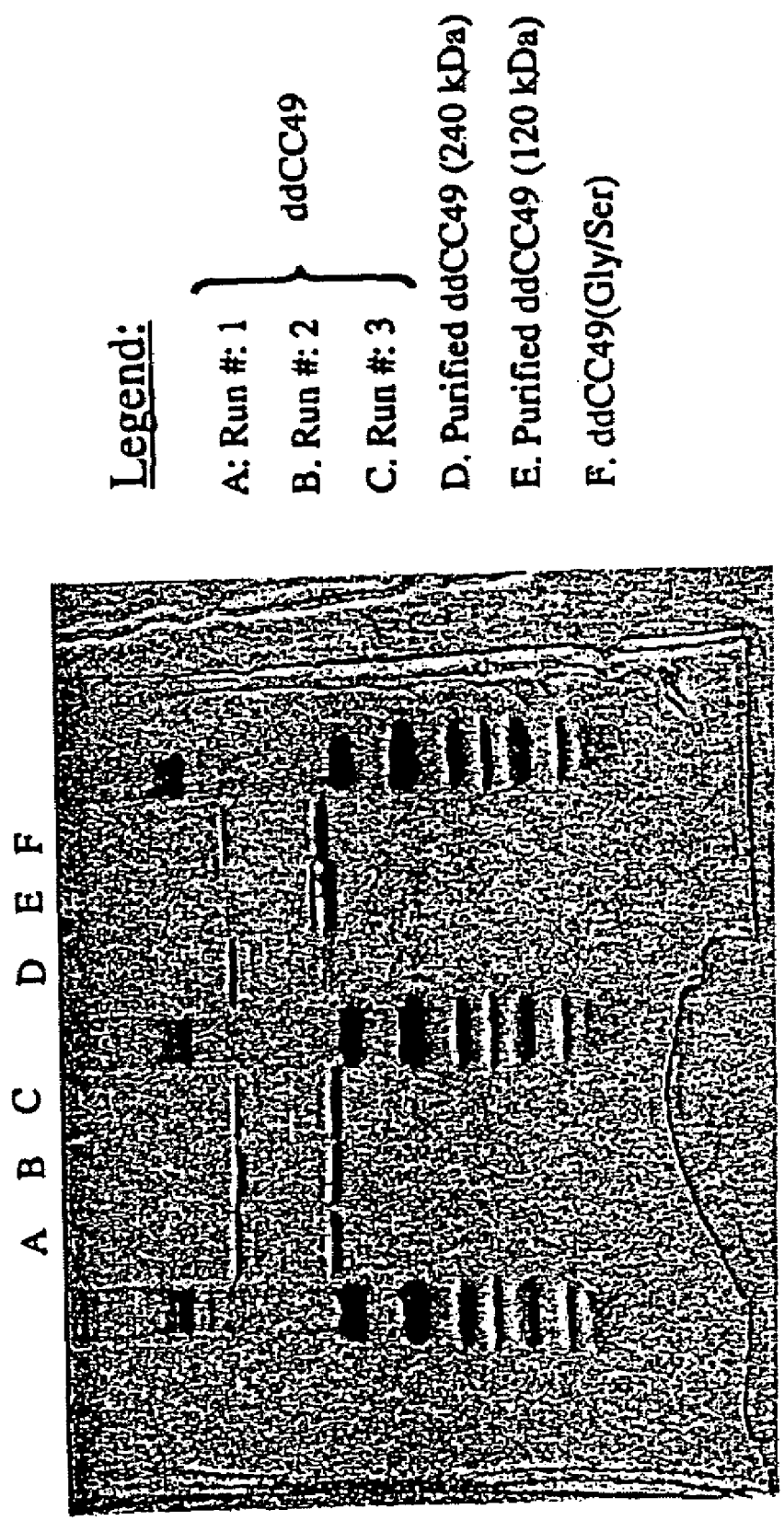
FIG. 10 is a representation of a SDS-PAGE of various preparations of the CC49.$\Delta C_H2$ construct showing purified forms of the monomeric variant and the dimeric variant as well as mixtures thereof.

While the present invention may be embodied in many different forms, disclosed herein are specific illustrative embodiments thereof that exemplify the principles of the invention. It should be emphasized that the present invention is not limited to the specific embodiments illustrated.

The present invention is predicted, at least in part, on the fact that antibodies which are immunoreactive with antigens associated with physiological disorders or abnormalities may be modified or altered to provide dimeric constructs having enhanced biochemical characteristics and improved efficacy when used in therapeutic protocols. In this regard it has surprisingly been found that standard antibodies, modified according to the present invention, form monomeric subunits which spontaneously assemble or associate non-covalently to form stable dimeric constructs. If the associated monomeric subunits are the same the resulting dimeric construct will have four identical binding sites and is termed a homodimer for the purposes of this application. Conversely, if the associated monomeric subunits are different (e.g. derived from separate antibodies) than the resulting dimeric construct will have two binding sites for one antigen and two binding sites for a second antigen and, for the purposes of this application will be termed a heterodimer. In any event, the dimeric or tetravalent construct or antibody (four heavy chains and four light chains, $H_4L_4$) may be used as described in the instant application to treat a variety of disorders.

More specifically it has surprisingly been found that monomeric subunits (e.g. modified antibodies) will spontaneously assemble to form stable tetravalent antibodies held together through non-covalent interactions. While not wishing to be bound by any particular theory, it appears that modification of the constant region of standard antibodies can provide modified antibodies that associate though non-covalent interactions in the constant region to provide durable dimeric or tetravalent constructs. For example, in specific embodiments of the present invention, deletion of all or part of the $C_H2$ region between the hinge and the $C_H3$ domain resulted in a bivalent molecule having a disulfide linked hinge region and a mismatched $C_H3$ domain. It is believed that these mismatched $C_H3$ domains on different neighboring molecules align and interact non-covalently to provide the stable tetravalent antibodies of the present invention. The resulting dimeric construct was recovered and purified to provide a novel 240 kDa, ($H_4L_4$) tetravalent molecule. Advantageously such constructs do not have problems with excessive immunogenicity often associated with chemically formed tetravalent antibodies. Moreover, unlike dimeric molecules formed by random chemical linkages that may hinder one or more binding sites, the dimeric constructs of the present invention maintain high binding affinities due to their association being limited to the constant region. These constructs also display a relatively short circulatory half-life that may reduce myelotoxicity when they are used in a radioimmunotherapeutic (RIT) setting. As such, the tetravalent antibodies of the instant invention are particularly useful in therapeutic and diagnostic applications.

As discussed in more detail below the term "modified antibody" shall be held to mean any antibody, or binding fragment or recombinant thereof, immunoreactive with a tumor associated antigen in which at least a fraction of one or more of the constant region domains has been deleted or otherwise altered so as to provide desired biochemical characteristics such as non-covalent association with similar molecules, increased tumor localization or reduced serum half-life when compared with a whole, unaltered antibody of approximately the same binding specificity. In preferred embodiments, the modified antibodies of the present invention have at least a portion of one of the constant domains deleted. Such constructs shall be termed "domain deleted antibodies" for the purposes of the instant disclosure. More preferably, one entire domain of the constant region of the modified antibody will be deleted and even more preferably the entire $C_H2$ domain will be deleted. As discussed herein, each of the desired variants may readily be fabricated or constructed from a whole precursor or parent antibody using well known techniques.

Besides the other advantages, the fact that the dimeric constructs of the present invention are associated almost exclusively through their constant regions allows them to retain their natural binding specificity. However, they exhibit an enhanced binding affinity when compared with conventional antibodies because of the number of binding sites with the proximity of the cell surface or other matrix exhibiting multiple antigen copies. This advantage of the present invention is shown in Table 1 immediately below which summarizes the binding data (ED50) of various constructs all having the same variable region.

TABLE 1

| Humanized CC49 | IgG | Kd = 2.5 nM |
|---|---|---|
| ddCC49 | Gly/Ser spacer | Kd = 1.8 nM |
| ddCC49 | No spacer | Kd = 0.8 nM |
| ddCC49 | No Spacer (120 kDa Variant) | Kd = 2.3 nM |
| ddCC49 | No Spacer (240 kDa Variant) | Kd = 0.1 nM |

As may be seen in Table 1, the dimeric assemblies of the domain deleted modified antibody (ddCC49) have a binding affinity on an order of magnitude greater than that of the naturally occurring IgG or constructs that do not dimerize. These properties and ease of production provide distinct advantages that allow the constructs of the present invention to be used in a number of situations. For example:

Dimererized constructs of MAb that are tetravalent and have high affinity binding are useful for non-radioactive applications where increased binding or hyper cross-linking of membrane antigens are important for inducing biological activity;

The genetically engineered dimers of the present invention offer an advantage over chemical dimers in that they are produced using molecular mechanisms and therefore cheaper to obtain with higher yields. They also maintain high binding affinity, which may be reduced after chemical conjugation strategies;

The disclosed genetically engineered dimers, due to their increased binding affinity over monomeric constructs, would be useful in therapeutic applications which do not require cell depletion or killing but require blocking of the target antigen such as to prevent a ligand/receptor interaction. Exemplary uses would be blocking of CD4 cells using an anti-CD4 antibody or B7 interactions either by blocking B7 or its T-cell receptor, CTLA-4 or CD80. Other examples could include blocking the CD23 antigen using a dimeric version of IDEC 152 (an anti-CD23 antibody) or blocking the CD40-CD40L interaction using a dimeric version of IDEC 131 (an anti-CD40L antibody); and The dimeric constructs would also have therapeutic application in viral or bacterial neutralization, given their high binding affinity over monomeric antibodies and their rapid accumulation and digestion in the liver. Many example can be considered including anti-RSV antibodies, anti-HPV antibodies and anti-HIV antibodies.

In addition to the uses enumerated above, those skilled in the art will appreciate that the compounds, compositions and methods of the present invention are particularly useful for treating a variety of disorders including neoplastic disorders or immune (including autoimmune) disorders. In this regard the present invention may be used to treat any neoplastic disorder, tumor or malignancy that exhibits a tumor associated antigen. Similarly, the methods and compositions may be used to treat any autoimmune disorder or anomaly caused in whole or in part by a cell population exhibiting an autoantigen.

As discussed above, the dimeric antibodies of the present invention may be immunoreactive with one or more tumor antigens or antigens associated with immune disorders. For neoplastic disorders, the antigen binding portion (i.e. the variable region or immunoreactive fragment or recombinant thereof) of the disclosed dimeric antibodies binds to a selected tumor associated antigen at the site of the malignancy. Similarly, in immune (including autoimmune) disorders the disclosed tetravalent antibodies will bind to selected markers on the offending cells. Given the number of reported antigens associated with neoplasms and immune disorders, and the number of related antibodies, those skilled in the art will appreciate that the presently disclosed dimeric antibodies may therefore be derived from any one of a number of whole antibodies. More generally, dimeric antibodies useful in the present invention may be obtained or derived from any antibody (including those previously reported in the literature) that reacts with an antigen or marker associated with the selected condition. Further, the parent or precursor antibody, or fragments thereof, used to generate the disclosed dimeric antibodies may be murine, human, chimeric, humanized, non-human primate or primatized. In other preferred embodiments the dimeric antibodies of the present invention may comprise single chain antibody constructs (such as that disclosed in U.S. Pat. No. 5,892,019 which is incorporated herein by reference) having altered constant domains as described herein. Consequently, any of these types of antibodies modified in accordance with the teachings herein is compatible with the instant invention.

As used herein, "tumor associated antigens" means any antigen which is generally associated with tumor cells, i.e., occurring at the same or to a greater extent as compared with normal cells. More generally, tumor associated antigens comprise any antigen that provides for the localization of immunoreactive antibodies at a neoplastic cell irrespective of its expression on non-malignant cells. Such antigens may be relatively tumor specific and limited in their expression to the surface of malignant cells. Alternatively, such antigens may be found on both malignant and non-malignant cells. For example, CD20 is a pan B antigen that is found on the surface of both malignant and non-malignant B cells that has proved to be an extremely effective target for immunotherapeutic antibodies for the treatment of non-Hodgkin's lymphoma. In this respect, pan T cell antigens such as CD2, CD3, CD5, CD6 and CD7 also comprise tumor associated antigens within the meaning of the present invention. Still other exemplary tumor associated antigens comprise but not limited to MAGE-1, MAGE-3, MUC-1, HPV 16, HPV E6 & E7, TAG-72, CEA, L6-Antigen, CD19, CD22, CD37, CD52, HLA-DR, EGF Receptor and HER2 Receptor. In many cases immunoreactive antibodies for each of these antigens have been reported in the literature. Those skilled in the art will appreciate that each of these antibodies may serve as a precursor for modified antibodies in accordance with the present invention.

The dimeric antibodies of the present invention preferably associate with, and bind to, tumor or immune associated antigens as described above. Accordingly, as will be discussed in some detail below the dimeric antibodies of the present invention may be derived, generated or fabricated from any one of a number of antibodies that react with tumor associated antigens. In preferred embodiments the monomeric subunits of the tetravalent antibodies are modified or domain deleted antibodies that are derived using common genetic engineering techniques whereby at least a portion of one or more constant region domains are deleted or altered so as to provide the desired biochemical characteristics such as reduced serum half-life. More particularly, as will be exemplified below, one skilled in the art may readily isolate the genetic sequence corresponding to the variable and/or constant regions of the subject antibody and delete or alter the appropriate nucleotides to provide modified antibodies for use as monomeric subunits in accordance with the instant invention. It will further be appreciated that compatible modified antibodies may be expressed and produced on a clinical or commercial scale using well-established protocols.

In selected embodiments, modified antibodies useful in the present invention will be derived from known antibodies to antigens associated with neoplasms or immune disorders (e.g. autoantigens). This may readily be accomplished by obtaining either the nucleotide or amino acid sequence of the parent antibody and engineering the modifications as discussed herein. For other embodiments it may be desirable to only use the antigen binding region (e.g., variable region or complementary determining regions) of the known antibody and combine them with a modified constant region to produce the desired modified antibodies that may then be used to assemble the disclosed tetravalent constructs. Compatible single chain monomeric subunits may be generated in a similar manner. In any event, it will be appreciated that the tetravalent antibodies of the present invention may also be engineered to improve affinity or reduce immunogenicity as is common in the art. For example, the dimeric antibodies of the present invention may be derived or fabricated from antibodies that have been humanized or chimerized. Thus, dimeric antibodies consistent with present invention may be derived or assembled from and/or comprise naturally occurring murine, primate (including human) or other mammalian monoclonal antibodies, chimeric antibodies, humanized antibodies, primatized antibodies, bispecific antibodies or single chain antibody constructs as well as immunoreactive fragments of each type.

As alluded to above, previously reported antibodies that react with tumor associated antigens may be altered as described herein to provide the dimeric antibodies of the present invention. Exemplary antibodies that may be used to provide antigen binding regions for, generate or derive the disclosed dimeric antibodies include, but are not limited to Y2B8 and C2B8 (Zevalin™ & Rituxan®, IDEC Pharmaceuticals Corp., San Diego), Lym 1 and Lym 2 (Techniclone), LL2 (Immunomedics Corp., New Jersey), HER2 (Herceptin®, Genentech Inc., South San Francisco), B1 (Bexxar®, Coulter Pharm., San Francisco), Campath® (Millennium Pharmaceuticals, Cambridge) MB1, BH3, B4, B72.3 (Cytogen Corp.), CC49 (National Cancer Institute) and 5E10 (University of Iowa). In preferred embodiments, the dimeric antibodies of the present invention will bind to the same tumor associated antigens as the antibodies enumerated immediately above. In particularly preferred embodiments, the dimeric antibodies will be derived from or bind the same antigens as Y2B8, C2B8, CC49 and C5E10 and, even more preferably, will comprise domain deleted antibodies (i.e., $\Delta C_H2$ antibodies).

In a first preferred embodiment, the tetravalent antibody will bind to the same tumor associated antigen as Rituxan®. Rituxan (also known as, IDEC-C2B8 and C2B8) was the first FDA-approved monoclonal antibody for treatment of human B-cell lymphoma (see U.S. Pat. Nos. 5,843,439; 5,776,456 and 5,736,137 each of which is incorporated herein by reference). Y2B8 is the murine parent of C2B8. Rituxan is a chimeric, anti-CD20 monoclonal antibody which is growth inhibitory and reportedly sensitizes certain lymphoma cell lines for apoptosis by chemotherapeutic agents in vitro. The antibody efficiently binds human complement, has strong FcR binding, and can effectively kill human lymphocytes in vitro via both complement dependent (CDC) and antibody-dependent (ADCC) mechanisms (Reff et al., Blood 83: 435-445 (1994)). Those skilled in the art will appreciate that dimeric variants (homodimers or heterodimers) of C2B8 or Y2B8, modified according to the instant disclosure, may be used in conjugated or unconjugated forms to effectively treat patients presenting with CD20+ malignancies. More generally, it must be reiterated that the modified antibodies disclosed herein may be used in either a "naked" or unconjugated state or conjugated to a cytotoxic agent to effectively treat any one of a number of disorders.

In other preferred embodiments of the present invention, the tetravalent antibody will be derived from, or bind to, the same tumor associated antigen as CC49. As previously alluded to, CC49 binds human tumor associated antigen TAG-72 which is associated with the surface of certain tumor cells of human origin, specifically the LS174T tumor cell line. LS174T [American Type Culture Collection (herein ATCC) No. CL 188] is a variant of the LS180 (ATCC No. CL 187) colon adenocarcinoma line.

It will further be appreciated that numerous murine monoclonal antibodies have been developed which have binding specificity for TAG-72. One of these monoclonal antibodies, designated B72.3, is a murine IgG1 produced by hybridoma B72.3 (ATCC No. HB-8108). B72.3 is a first generation monoclonal antibody developed using a human breast carcinoma extract as the immunogen (see Colcher et al., Proc. Natl. Acad. Sci. (USA), 78:3199-3203 (1981); and U.S. Pat. Nos. 4,522,918 and 4,612,282 each of which is incorporated herein by reference). Other monoclonal antibodies directed against TAG-72 are designated "CC" (for colon cancer). As described by Schlom et al. (U.S. Pat. No. 5,512,443 which is incorporated herein by reference) CC monoclonal antibodies are a family of second generation murine monoclonal antibodies that were prepared using TAG-72 purified with B72.3. Because of their relatively good binding affinities to TAG-72, the following CC antibodies have been deposited at the ATCC, with restricted access having been requested: CC49 (ATCC No. HB 9459); CC 83 (ATCC No. HB 9453); CC46 (ATCC No. HB 9458); CC92 (ATCC No. HB 9454); CC30 (ATCC No. HB 9457); CC11 (ATCC No. 9455); and CC15 (ATCC No. HB 9460). U.S. Pat. No. 5,512,443 further teaches that the disclosed antibodies may be altered into their chimeric form by substituting, e.g., human constant regions (Fc) domains for mouse constant regions by recombinant DNA techniques known in the art. Besides disclosing murine and chimeric anti-TAG-72 antibodies. Schlom et al. have also produced variants of a humanized CC49 antibody as disclosed in PCT/US99/25552 and single chain constructs as disclosed in U.S. Pat. No. 5,892,019 each of which is also incorporated herein by reference. Those skilled in the art will appreciate that each of the foregoing antibodies, constructs or recombinants, and variations thereof, may be modified and used to provide tetravalent antibodies in accordance with the present invention.

Besides the anti-TAG-72 antibodies discussed above, various groups have also reported the construction and partial characterization of domain-deleted CC49 and B72.3 antibodies (e.g., Calvo et al. Cancer Biotherapy, 8(1):95-109 (1993), Slavin-Chiorini et al. Int. J. Cancer 53:97-103 (1993) and Slavin-Chiorini et al. Cancer. Res. 55:5957-5967 (1995)). It should be appreciated that the disclosed constructs may be modified and used to provide tetravalent antibodies that are compatible with the methods and compositions of the present invention.

Still other preferred embodiments of the present invention comprise modified antibodies that are derived from or bind to the same tumor associated antigen as C5E10. As set forth in U.S. Pat. No. 6,207,805, C5E10 is an antibody that recognizes a glycoprotein determinant of approximately 115 kDa that appears to be specific to prostate tumor cell lines (e.g. DU145, PC3, or ND1). Thus, in conjunction with the present invention, modified antibodies (e.g., $C_H2$ domain-deleted antibodies) that specifically bind to the same tumor associated antigen recognized by C5E10 antibodies could be produced, assemble to form tetravalent antibodies and used in a conjugated or unconjugated form for the treatment of neoplastic disorders. In particularly preferred embodiments, the modified antibody will be derived or comprise all or part of the antigen binding region of the C5E10 antibody as secreted from the hybridoma cell line having ATCC accession No. PTA-865. The resulting modified antibody could then be conjugated to a radionuclide as described below and administered to a patient suffering from prostate cancer in accordance with the methods herein.

In addition to the antibodies discussed above, it may be desirable to provide tetravalent assemblies comprising modified antibodies derived from or comprising antigen binding regions of novel antibodies generated using immunization coupled with common immunological techniques. Using art recognized protocols, antibodies are preferably raised in mammals by multiple subcutaneous or intraperitoneal injections of the relevant antigen (e.g., purified tumor associated antigens or cells or cellular extracts comprising such antigens) and an adjuvant. This immunization typically elicits an immune response that comprises production of antigen-reactive antibodies from activated splenoyctes or lymphocytes. While the resulting antibodies may be harvested from the serum of the animal to provide polyclonal preparations, it is often desirable to isolate individual lymphocytes from the spleen, lymph nodes or peripheral blood, to provide homogenous preparations of monoclonal antibodies (MAbs). Preferably, the lymphocytes are obtained from the spleen.

In this well known process (Kohler et al., *Nature*, 256:495 (1975)) the relatively short-lived, or mortal, lymphocytes from a mammal which has been injected with antigen are fused with an immortal tumor cell line (e.g. a myeloma cell line), thus producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They therefore produce antibodies which are homogenous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by immunoprecipitation or by an in vitro assay, such as a radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice*, pp 59-103 (Academic Press, 1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In other compatible embodiments, DNA encoding the desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be modified as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification thereof by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Those skilled in the art will also appreciate that DNA encoding antibodies or antibody fragments may also be derived from antibody phage libraries as set forth, for example, in EP 368 684 B1 and U.S. Pat. No. 5,969,108 each of which is incorporated herein by reference. Several publications (e.g., Marks et al. *Bio/Technology* 10:779-783 (1992)) have described the production of high affinity human antibodies by chain shuffling, as well as combinatorial infection and in vivo recombination as a strategy for constructing large phage libraries. Such procedures provide viable alternatives to traditional hybridoma techniques for the isolation and subsequent cloning of monoclonal antibodies and, as such, are clearly within the purview of the instant invention.

Yet other embodiments of the present invention comprise the generation of substantially human antibodies in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array in such germ line mutant mice will result in the production of human antibodies upon antigen challenge. Another preferred means of generating human antibodies using SCID mice is disclosed in commonly-owned, co-pending U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology*, 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

As is apparent from the instant specification, genetic sequences useful for producing the dimeric antibodies of the present invention may be obtained from a number of different sources. For example, as discussed extensively above, a variety of human antibody genes are available in the form of publicly accessible deposits. Many sequences of antibodies and antibody-encoding genes have been published and suitable antibody genes can be synthesized from these sequences much as previously described. Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

It will further be appreciated that the scope of this invention further encompasses all alleles, variants and mutations of the DNA sequences described herein.

As is well known, RNA may be isolated from the original hybridoma cells or from other transformed cells by standard techniques, such as quanidinium isothiocyanate extraction and precipitation followed by centrifugation or chromatography. Where desirable, mRNA may be isolated from total RNA by standard techniques such as chromatography on oligodT cellulose. Techniques suitable to these purposes are familiar in the art and are described in the foregoing references.

cDNAs that encode the light and the heavy chains of the antibody may be made, either simultaneously or separately, using reverse transcriptase and DNA polymerase in accordance with well known methods. It may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells as described herein, restriction mapped and sequenced in accordance with standard, well known techniques set forth in detail in the foregoing references relating to recombinant DNA techniques. Of course, the DNA may be modified according to the present invention at any point during the isolation process or subsequent analysis.

Preferred antibody sequences are disclosed herein. Oligonucleotide synthesis techniques compatible with this aspect of the invention are well known to the skilled artisan and may be carried out using any of several commercially available automated synthesizers. In addition, DNA sequences encoding several types of heavy and light chains set forth herein can be obtained through the services of commercial DNA synthesis vendors. The genetic material obtained using any of the foregoing methods may then be altered or modified to provide antibodies compatible with the present invention.

While a variety of different types of antibodies may be obtained and modified according to the instant invention, modified antibodies used to assemble the dimeric constructs of the instant invention will share various common traits. To that end, the term "immunoglobulin" shall be held to refer to a combination of two heavy and two light chains ($H_2L_2$) whether or not it possesses any relevant specific immunoreactivity. "Antibodies" refers to such assemblies which have significant known specific immunoreactive activity to an antigen (e.g. a tumor associated antigen), comprising light and heavy chains, with or without covalent linkage between them. As discussed above, "modified antibodies" according to the present invention are held to mean immunoglobulins, antibodies, or immunoreactive fragments or recombinants thereof, in which at least a fraction of one or more of the constant region domains has been deleted or otherwise altered so as to provide desired biochemical characteristics such as the ability to non-covalently dimerize, increased tumor localization or reduced serum half-life when compared with a whole, unaltered antibody of approximately the same immunogenicity. For the purposes of the instant application, immunoreactive single chain antibody constructs having altered or omitted constant region domains may be considered to be modified antibodies. As discussed above, preferred modified antibodies or domain deleted antibodies of the present invention have at least a portion of one of the constant domains deleted. More preferably, one entire domain of the constant region of the modified antibody will be deleted and even more preferably the entire $C_H2$ domain will be deleted.

Basic immunoglobulin structures in vertebrate systems are relatively well understood. As will be discussed in more detail below, the generic term "immunoglobulin" comprises five distinct classes of antibody that can be distinguished biochemically. While all five classes are clearly within the scope of the present invention, the following discussion will generally be directed to the class of IgG molecules. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

More specifically, both the light and heavy chains are divided into regions of structural and functional homology. The terms "constant" and "variable" are used functionally. In this regard, it will be appreciated that the variable domains of both the light ($V_L$) and heavy ($V_H$) chains determine antigen recognition and specificity. Conversely, the constant domains of the light chain ($C_L$) and the heavy chain ($C_H1$, $C_H2$ or $C_H3$) confer important biological properties such as secretion, transplacental mobility, Fc receptor binding, complement binding, and the like. By convention the numbering of the constant region domains increases as they become more distal from the antigen binding site or amino-terminus of the antibody. Thus, the $C_H3$ and $C_L$ domains actually comprise the carboxy-terminus of the heavy and light chains respectively.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. At the N-terminus is a variable region and at the C-terminus is a constant region. Those skilled in the art will appreciate that heavy chains are classified as gamma, mu, alpha, delta, or epsilon, (γ, μ, α, δ, ε) with some subclasses among them. It is the nature of this chain that determines the "class" of the antibody as IgA, IgD, IgE IgG, or IgM. The immunoglobulin subclasses (isotypes) e.g. $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the purview of the instant invention.

As indicated above, the variable region allows the antibody to selectively recognize and specifically bind epitopes on immunoreactive antigens. That is, the $V_L$ domain and $V_H$ domain of an antibody combine to form the variable region that defines a three dimensional antigen binding site. This quaternary antibody structure provides for an antigen binding site present at the end of each arm of the Y. More specifically, the antigen binding site is defined by three complementary determining regions (CDRs) on each of the $V_H$ and $V_L$ chains. Of course, the dimeric assemblies disclosed herein may be likened to two associated Ys ($H_4L_4$) so there will be four binding sites. Hence the term "tetravalent" antibodies.

The six CDRs present on each monomeric antibody ($H_2L_2$) are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops connecting, and in some cases forming part of, the β-sheet structure. Thus, these framework regions act to form a scaffold that provides for positioning the six CDRs in correct orientation by inter-chain, non-covalent interactions. In any event, the antigen binding site formed by the positioned CDRs defines a surface complementary to the epitope on the immunoreactive antigen. This complementary surface promotes the non-covalent binding of the antibody to the immunoreactive antigen epitope.

For the purposes of the present invention, it should be appreciated that disclosed modified antibodies capable of forming dimeric constructs may comprise any type of variable region that provides for the association of the homodimer or heterodimer with the selected antigen. In this regard, the variable region may comprise or be derived from any type of mammal that can be induced to mount a humoral response and generate immunoglobulins against the desired antigen. As such, the variable region of the modified antibodies may be, for example, of human, murine, non-human primate (e.g. cynomolgus monkeys, macaques, etc.) or lupine origin. In particularly preferred embodiments both the variable and constant regions of compatible modified antibodies are human. In other selected embodiments the variable regions of compatible antibodies (usually derived from a non-human source) may be engineered or specifically tailored to improve the binding properties or reduce the immunogenicity of the molecule. In this respect, variable regions useful in the present invention may be humanized or otherwise altered through the inclusion of important DNA or amino acid sequences.

For the purposes of the instant application the term "humanized antibody" shall mean an antibody derived from a non-human antibody, typically a murine antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81: 6851-5 (1984); Morrison et al., *Adv. Immunol.* 44: 65-92 (1988); Verhoeyen et al., *Science* 239: 1534-1536 (1988); Padlan, *Molec. Immun.* 28: 489-498 (1991); Padlan, *Molec. Immun.* 31: 169-217 (1994), and U.S. Pat. Nos. 5,585,089, 5,693,761 and 5,693,762 all of which are hereby incorporated by reference in their entirety.

Those skilled in the art will appreciate that the technique set forth in option (a) above will produce "classic" chimeric antibodies. In the context of the present application the term "chimeric antibodies" will be held to mean any antibody wherein the immunoreactive region or site is obtained or derived from a first species and the constant region (which may be intact, partial or modified in accordance with the instant invention) is obtained form a second species. In preferred embodiments the antigen binding region or site will be from a non-human source (e.g. mouse) and the constant region is human. While the immunogenic specificity of the variable region is not generally affected by its source, a human constant region is less likely to elicit an immune response from a human subject than would the constant region from a non-human source.

Preferably, the variable domains in both the heavy and light chains are altered by at least partial replacement of one or more CDRs and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. It must be emphasized that it may not be necessary to replace all of the CDRs with the complete CDRs from the donor variable region to transfer the antigen binding capacity of one variable domain to another. Rather, it may only be necessary to transfer those residues that are necessary to maintain the activity of the antigen binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that modified antibodies compatible with the instant invention will comprise antibodies, or immunoreactive fragments thereof, in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In preferred embodiments, the constant region of the modified antibodies will comprise a human constant region. Modifications to the constant region compatible with the instant invention comprise additions, deletions or substitutions of one or more amino acids in one or more domains. That is, the modified antibodies disclosed herein may comprise alterations or modifications to one or more of the three heavy chain constant domains ($C_H1$, $C_H2$ or $C_H3$) and/or to the light chain constant domain ($C_L$). As will be discussed in more detail below and shown in the examples, preferred embodiments of the invention comprise modified constant regions wherein one or more domains are partially or entirely deleted ("domain deleted antibodies"). In especially preferred embodiments compatible modified antibodies will comprise domain deleted constructs or variants wherein the entire $C_H2$ domain has been removed ($\Delta C_H2$ constructs). For other preferred embodiments a short amino acid spacer may be substituted for the deleted domain to provide flexibility and freedom of movement for the variable region.

As previously indicated, the subunit structures and three dimensional configuration of the constant regions of the various immunoglobulin classes are well known. For example, the $C_H2$ domain of a human IgG Fc region usually extends from about residue 231 to residue 340 using conventional numbering schemes. The $C_H2$ domain is unique in that it is not closely paired with another domain. Rather, two N-linked branched carbohydrate chains are interposed between the two $C_H2$ domains of an intact native IgG molecule. It is also well documented that the $C_H3$ domain extends from the $C_H2$ domain to the C-terminal of the IgG molecule and comprises approximately 108 residues while the hinge region of an IgG molecule joins the $C_H2$ domain with the $C_H1$ domain. This hinge region encompasses on the order of 25 residues and is flexible, thereby allowing the two N-terminal antigen binding regions to move independently.

Besides their configuration, it is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and may also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. Although various Fc receptors and receptor sites have been studied to a certain extent, there is still much which is unknown about their location, structure and functioning.

As discussed above, the modification of the constant region as described herein allows the disclosed modified antibodies to spontaneously assemble or associate into stable dimeric constructs or tetravalent antibodies. Moreover, while not limiting the scope of the present invention, it is believed that antibodies comprising constant regions modified as described herein provide for altered effector functions that, in turn, affect the biological profile of the administered antibody. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate compliment binding and thus reduce the serum half life and nonspecific association of a conjugated cytotoxin. Yet other modifications of the constant region may be used to eliminate disulfide linkages or oligosaccharide moieties that allow for enhanced localization due to increased antigen specificity or antibody flexibility. More generally, those skilled in the art will realize that antibodies modified as described herein may exert a number of subtle effects that may or may not be readily appreciated. However the resulting physiological profile, bioavailability and other biochemical effects of the modifications, such as tumor localization and serum half-life, may easily be measured and quantified using well know immunological techniques without undue experimentation.

Similarly, modifications to the constant region in accordance with the instant invention may easily be made using well known biochemical or molecular engineering techniques well within the purview of the skilled artisan. In this respect the examples appended hereto provide various constructs having constant regions modified in accordance with the present invention. More specifically, the exemplified constructs comprise chimeric and humanized antibodies having human constant regions that have been engineered to delete the $C_H2$ domain. Those skilled in the art will appreciate that such constructs are particularly preferred due to the regulatory properties of the $C_H2$ domain on the catabolic rate of the antibody.

$\Delta C_H2$ domain deleted antibodies set forth in the examples and the Figures are derived from the chimeric C2B8 antibody which is immunospecific for the CD20 pan B cell antigen and the humanised CC49 antibody which is specific for the TAG 72 antigen. As discussed in more detail below, both domain deleted constructs were derived from a proprietary vector (IDEC Pharmaceuticals, San Diego) encoding an IgG$_1$ human constant domain. Essentially, the vector was engineered to delete the $C_H2$ domain and provide a modified vector expressing a domain deleted IgG$_1$ constant region. Genes encoding the murine variable region of the C2B8 antibody or the variable region of the humanized CC49 antibody were then inserted in the modified vector and cloned. When expressed in transformed cells, these vectors provided huCC49.$\Delta C_H2$ or C2B$_8$.$\Delta C_H2$ respectively. As illustrated below, these constructs exhibited a number of properties that make them particularly attractive candidates for monomeric subunits.

It will be noted that the foregoing exemplary constructs were engineered to fuse the $C_H3$ domain directly to the hinge region of the respective modified antibodies. In other constructs it may be desirable to provide a peptide spacer between the hinge region and the modified $C_H2$ and/or $C_H3$ domains. For example, compatible constructs could be expressed wherein the $C_H2$ domain has been deleted and the remaining $C_H3$ domain (modified or unmodified) is joined to the hinge region with a 5-20 amino acid spacer. Such a spacer may be added, for instance, to ensure that the regulatory elements of the constant domain remain free and accessible or that the hinge region remains flexible. However, it should be noted that amino acid spacers may, in some cases, prove to be immunogenic or inhibit the desired dimerization of the monomeric subunits. For example, a domain deleted CC49 construct having a short amino acid spacer GGSSGGGGSG (SEQ ID NO: 17) substituted for the $C_H2$ domain (CC49.$\Delta C_H2$ [gly/ser]) is used as a control in the examples because it does not assemble spontaneously into a dimeric form. Accordingly, any spacer compatible with the instant invention will be relatively non-immunogenic and not inhibit the non-covalent association of the modified antibodies.

Besides the deletion of whole constant region domains, it will be appreciated that dimeric constructs of the present invention may be provided by the partial deletion or substitution of a few or even a single amino acid as long as it permits the desired non-covalent association between the monomeric subunits. For example, the mutation of a single amino acid in selected areas of the $C_H2$ domain may be enough to substantially reduce Fc binding and thereby increase tumor localization. Similarly, it may be desirable to simply delete that part of one or more constant region domains that control the effector function (e.g. complement CLQ binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other preferred embodiments may comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

Following manipulation of the isolated genetic material to provide modified antibodies as set forth above, the genes are typically inserted in an expression vector for introduction into host cells that may be used to produce the desired quantity of modified antibody that, in turn, provides the claimed dimeric constructs.

The term "vector" or "expression vector" is used herein for the purposes of the specification and claims, to mean vectors used in accordance with the present invention as a vehicle for introducing into and expressing a desired gene in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

In particularly preferred embodiments the cloned variable region genes are inserted into an expression vector along with the heavy and light chain constant region genes (preferably human) modified as discussed above. Preferably, this is effected using a proprietary expression vector of IDEC, Inc., referred to as NEOSPLA. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. As seen in the examples below, this vector has been found to result in very high level expression of antibodies upon incorporation of variable and constant region genes, transfection in CHO cells, followed by selection in G418 containing medium and methotrexate amplification. This vector system is substantially disclosed in commonly assigned U.S. Pat. Nos. 5,736,137 and 5,658,570, each of which is incorporated by reference in its entirety herein. This system provides for high expression levels, i.e., >30 pg/cell/day.

In other preferred embodiments the modified antibodies of the instant invention may be expressed using polycistronic constructs such as those disclosed in copending U.S. provisional application No. 60/331,481 filed Nov. 16, 2001 and incorporated herein in its entirety. In these novel expression systems, multiple gene products of interest such as heavy and light chains of antibodies may be produced from a single polycistronic construct. These systems advantageously use an internal ribosome entry site (IRES) to provide relatively high levels of modified antibodies in eukaryotic host cells. Compatible IRES sequences are disclosed in U.S. Pat. No. 6,193,980 which is also incorporated herein. Those skilled in the art will appreciate that such expression systems may be used to effectively produce the full range of modified antibodies disclosed in the instant application.

More generally, once the vector of DNA sequence encoding the monomeric subunit (e.g. modified antibody) has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electrophoration. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

As used herein, the term "transformation" shall be used in a broad sense to refer to any introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. As defined herein, antibodies or modifications thereof produced by a host cell that is, by virtue of this transformation, recombinant. In descriptions of processes for isolation of antibodies from recombinant hosts, the terms "cell" and "cell culture" are used interchangeably to denote the source of antibody unless it is clearly specified otherwise. In other words, recovery of antibody from the "cells" may mean either from spun down whole cells, or from the cell culture containing both the medium and the suspended cells.

The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CV1 (monkey kidney line), COS (a derivative of CV1 with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJ1 (human lymphocyte) and 293 (human kidney). CHO cells are particularly preferred. Host cell lines are typically available from commercial services, the American Tissue Culture Collection or from published literature.

In vitro production allows scale-up to give large amounts of the desired monomeric subunit and, by extension, dimeric constructs. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. As previously described, at least some of the monomeric subunits spontaneously associate non-covalently to form dimeric antibodies. For isolation and recovery of the dimeric antibodies, the immunoglobulins in the culture supernatants may first be concentrated, e.g. by precipitation with ammonium sulphate, dialysis against hygroscopic material such as PEG, filtration through selective membranes, or the like. If necessary and/or desired, the concentrated solutions of tetravalent antibodies are purified by the customary chromatography methods, for example gel filtration, ion-exchange chromatography, chromatography over DEAE-cellulose or (immuno)affinity chromatography.

Modified antibody genes can also be expressed non-mammalian cells such as bacteria or yeast. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli; Salmonella; Bacillaceae*, such as *Bacillus subtilis; Pneumococcus; Streptococcus*, and *Haemophilus influenzae*. It will further be appreciated that, when expressed in bacteria, the immunoglobulin heavy chains and light chains typically become part of inclusion bodies. The chains then must be isolated, purified and then assembled into functional monomeric subunits. The monomeric subunits will then self-assemble into tetravalent antibodies.

In addition to prokaryates, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the trp1 gene which provides a selection marker for a mutant strain of yeast lacking the ability to grow in tryptophan, for example ATCC No. 44076 or PEP4-1 (Jones, Genetics, 85:12 (1977)). The presence of the trp1 lesion as a characteristic of the yeast host cell genome then provides an effective environment for detecting transformation by growth in the absence of tryptophan.

Regardless of how clinically useful quantities are obtained, the dimeric antibodies of the present invention may be used in any one of a number of conjugated (i.e. an immunoconjugate) or unconjugated forms. In particular, the antibodies of the present invention may be conjugated to cytotoxins such as radioisotopes, therapeutic agents, cytostatic agents, biological toxins or prodrugs. Alternatively, the dimeric antibodies of the instant invention may be used in a nonconjugated or original form to harness the subject's natural defense mechanisms to eliminate the malignant cells. In particularly preferred embodiments, the modified antibodies may be conjugated to radioisotopes, such as $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re using anyone of a number of well known chelators or direct labeling. In other embodiments, the disclosed compositions may comprise modified antibodies coupled to drugs, prodrugs or biological response modifiers such as methotrexate, adriamycin, and lymphokines such as interferon. Still other embodiments of the present invention comprise the use of modified antibodies conjugated to specific biotoxins such as ricin or diptheria toxin. In yet other embodiments the modified antibodies may be complexed with other immunologically active ligands (e.g. antibodies or fragments thereof) wherein the resulting molecule binds to both the neoplastic cell and an effector cell such as a T cell. The selection of which conjugated or unconjugated modified antibody to use will depend of the type and stage of cancer, use of adjunct treatment (e.g., chemotherapy or external radiation) and patient condition. It will be appreciated that one skilled in the art could readily make such a selection in view of the teachings herein.

As used herein, "a cytotoxin or cytotoxic agent" means any agent that is detrimental to the growth and proliferation of cells and may act to reduce, inhibit or destroy a cell or malignancy when exposed thereto. Exemplary cytotoxins include, but are not limited to, radionuclides, biotoxins, enzymatically active toxins, cytostatic or cytotoxic therapeutic agents, prodrugs, immunologically active ligands and biological response modifiers such as cytokines. As will be discussed in more detail below, radionuclide cytotoxins are particularly preferred for use in the instant invention. However, any cytotoxin that acts to retard or slow the growth of immunoreactive cells or malignant cells or to eliminate these cells and may be associated with the dimeric antibodies disclosed herein is within the purview of the present invention.

It will be appreciated that, in previous studies, anti-tumor antibodies labeled with these isotopes have been used successfully to destroy cells in solid tumors as well as lymphomas/leukemias in animal models, and in some cases in humans. The radionuclides act by producing ionizing radiation which causes multiple strand breaks in nuclear DNA, leading to cell death. The isotopes used to produce therapeutic conjugates typically produce high energy α- or β-particles which have a short path length. Such radionuclides kill cells to which they are in close proximity, for example neoplastic cells to which the conjugate has attached or has entered. They have little or no effect on non-localized cells. Radionuclides are essentially non-immunogenic.

It will be appreciated that, in previous studies, anti-tumor antibodies labeled with isotopes have been used successfully to destroy cells in solid tumors as well as lymphomas/leukemias in animal models, and in some cases in humans. The radionuclides act by producing ionizing radiation which causes multiple strand breaks in nuclear DNA, leading to cell death. The isotopes used to produce therapeutic conjugates typically produce high energy α-, γ- or β-particles which have a therapeutically effective path length. Such radionuclides kill cells to which they are in close proximity, for example neoplastic cells to which the conjugate has attached or has entered. They generally have little or no effect on non-localized cells. Radionuclides are essentially non-immunogenic.

With respect to the use of radiolabeled conjugates in conjunction with the present invention, the modified antibodies may be directly labeled (such as through iodination) or may be labeled indirectly through the use of a chelating agent. As used herein, the phrases "indirect labeling" and "indirect labeling approach" both mean that a chelating agent is covalently attached to an antibody and at least one radionuclide is associated with the chelating agent. Such chelating agents are typically referred to as bifunctional chelating agents as they bind both the polypeptide and the radioisotope. Particularly preferred chelating agents comprise 1-isothiocyematobenzyl-3-methyldiothelene triamine-pentaacetic acid ("MX-DTPA") and cyclohexyl diethylenetriamine pentaacetic acid ("CHX-DTPA") derivatives. Other chelating agents comprise P-DOTA and EDTA derivatives. Particularly preferred radionuclides for indirect labeling include $^{111}$In and $^{90}$Y.

As used herein, the phrases "direct labeling" and "direct labeling approach" both mean that a radionuclide is covalently attached directly to a dimeric antibody (typically via an amino acid residue). More specifically, these linking technologies include random labeling and site-directed labeling. In the latter case, the labeling is directed at specific sites on the dimer or tetramer, such as the N-linked sugar residues present only on the Fc portion of the conjugates. Further, various direct labeling techniques and protocols are compatible with the instant invention. For example, Technetium-99m labelled tetravalent antibodies may be prepared by ligand exchange processes, by reducing pertechnate ($TcO_4$) with stannous ion solution, chelating the reduced technetium onto a Sephadex column and applying the antibodies to this column, or by batch labelling techniques, e.g. by incubating pertechnate, a reducing agent such as $SnCl_2$, a buffer solution such as a sodium-potassium phthalate-solution, and the antibodies. In any event, preferred radionuclides for directly labeling antibodies are well known in the art and a particularly preferred radionuclide for direct labeling is $^{131}I$ covalently attached via tyrosine residues. Modified antibodies according to the invention may be derived, for example, with radioactive sodium or potassium iodide and a chemical oxidising agent, such as sodium hypochlorite, chloramine T or the like, or an enzymatic oxidising agent, such as lactoperoxidase, glucose oxidase and glucose. However, for the purposes of the present invention, the indirect labeling approach is particularly preferred.

Patents relating to chelators and chelator conjugates are known in the art. For instance, U.S. Pat. No. 4,831,175 or Gansow is directed to polysubstituted diethylenetriaminepentaacetic acid chelates and protein conjugates containing the same, and methods for their preparation. U.S. Pat. Nos. 5,099,069, 5,246,692, 5,286,850, 5,434,287 and 5,124,471 of Gansow also relate to polysubstituted DTPA chelates. These patents are incorporated herein in their entirety. Other examples of compatible metal chelators are ethylenediaminetetraacetic acid (EDTA), diethylenetriaminepentaacetic acid (DPTA), 1,4,8,11-tetraazatetradecane, 1,4,8,11-tetraazatetradecane-1,4,8,11-tetraacetic acid, 1-oxa-4,7,12,15-tetraazaheptadecane-4,7,12,15-tetraacetic acid, or the like. Cyclohexyl-DTPA or CHX-DTPA is particularly preferred and is exemplified extensively below. Still other compatible chelators, including those yet to be discovered, may easily be discerned by a skilled artisan and are clearly within the scope of the present invention.

Compatible chelators, including the specific bifunctional chelator used to facilitate chelation in U.S. Pat. Nos. 6,682,734, 6,399,061, and 5,843,439, are preferably selected to provide high affinity for trivalent metals, exhibit increased tumor-to-non-tumor ratios and decreased bone uptake as well as greater in vivo retention of radionuclide at target sites, i.e., B-cell lymphoma tumor sites. However, other bifunctional chelators that may or may not possess all of these characteristics are known in the art and may also be beneficial in tumor therapy.

It will also be appreciated that, in accordance with the teachings herein, modified antibodies may be conjugated to different radiolabels for diagnostic and therapeutic purposes. To this end the aforementioned co-pending applications, herein incorporated by reference in their entirety, disclose radiolabeled therapeutic conjugates for diagnostic "imaging" of tumors before administration of therapeutic antibody. "In2B8" conjugate comprises a murine monoclonal antibody, 2B8, specific to human CD20 antigen, that is attached to $^{111}In$ via a bifunctional chelator, i.e., MX-DTPA (diethylenetriaminepentaacetic acid), which comprises a 1:1 mixture of 1-isothiocyanatobenzyl-3-methyl-DTPA and 1-methyl-3-isothiocyanatobenzyl-DTPA. $^{111}In$ is particularly preferred as a diagnostic radionuclide because between about 1 to about 10 mCi can be safely administered without detectable toxicity; and the imaging data is generally predictive of subsequent $^{90}Y$-labeled antibody distribution. Most imaging studies utilize 5 mCi $^{111}In$-labeled antibody, because this dose is both safe and has increased imaging efficiency compared with lower doses, with optimal imaging occurring at three to six days after antibody administration. See, for example, Murray, J. Nuc. Med. 26: 3328 (1985) and Carraguillo et al., J. Nuc. Med. 26: 67 (1985).

As indicated above, a variety of radionuclides are applicable to the present invention and those skilled in the art are credited with the ability to readily determine which radionuclide is most appropriate under various circumstances. For example, $^{131}I$ is a well known radionuclide used for targeted immunotherapy. However, the clinical usefulness of $^{131}I$ can be limited by several factors including: eight-day physical half-life; dehalogenation of iodinated antibody both in the blood and at tumor sites; and emission characteristics (e.g., large gamma component) which can be suboptimal for localized dose deposition in tumor. With the advent of superior chelating agents, the opportunity for attaching metal chelating groups to proteins has increased the opportunities to utilize other radionuclides such as $^{111}In$ and $^{90}Y$. $^{90}Y$ provides several benefits for utilization in radioimmunotherapeutic applications: the 64 hour half-life of $^{90}Y$ is long enough to allow antibody accumulation by tumor and, unlike e.g., $^{131}I$, $^{90}Y$ is a pure beta emitter of high energy with no accompanying gamma irradiation in its decay, with a range in tissue of 100 to 1,000 cell diameters. Furthermore, the minimal amount of penetrating radiation allows for outpatient administration of $^{90}Y$-labeled antibodies. Additionally, internalization of labeled antibody is not required for cell killing, and the local emission of ionizing radiation should be lethal for adjacent tumor cells lacking the target antigen.

Effective single treatment dosages (i.e., therapeutically effective amounts) of $^{90}Y$-labeled modified antibodies range from between about 5 and about 75 mCi, more preferably between about 10 and about 40 mCi. Effective single treatment non-marrow ablative dosages of $^{131}I$-labeled antibodies range from between about 5 and about 70 mCi, more preferably between about 5 and about 40 mCi. Effective single treatment ablative dosages (i.e., may require autologous bone marrow transplantation) of $^{131}I$-labeled antibodies range from between about 30 and about 600 mCi, more preferably between about 50 and less than about 500 mCi. In conjunction with a chimeric antibody, owing to the longer circulating half life vis-á-vis murine antibodies, an effective single treatment non-marrow ablative dosages of iodine-131 labeled chimeric antibodies range from between about 5 and about 40 mCi, more preferably less than about 30 mCi. Imaging criteria for, e.g., the $^{111}In$ label, are typically less than about 5 mCi.

While a great deal of clinical experience has been gained with $^{131}I$ and $^{90}Y$, other radiolabels are known in the art and have been used for similar purposes. Still other radioisotopes are used for imaging. For example, additional radioisotopes which are compatible with the scope of the instant invention include, but are not limited to, $^{123}I$, $^{125}I$, $^{33}P$, $^{57}Co$, $^{64}Cu$, $^{67}Cu$, $^{77}Br$, $^{81}Rb$, $^{81}Kr$, $^{87}Sr$, $^{113}In$, $^{127}Cs$, $^{129}Cs$, $^{132}I$, $^{197}Hg$, $^{203}Pb$, $^{206}Bi$, $^{177}Lu$, $^{186}Re$, $^{212}Pb$, $^{212}Bi$, $^{47}Sc$, $^{105}Rh$, $^{109}Pd$, $^{153}Sm$, $^{188}Re$, $^{199}Au$, $^{225}Ac$, $^{211}At$, and $^{213}Bi$. In this respect alpha, gamma and beta emitters are all compatible with in the instant invention. Further, in view of the instant disclosure it is submitted that one skilled in the art could readily determine which radionuclides are compatible with a selected course of treatment without undue experimentation. To this end, additional radionuclides which have already been used in clinical diagnosis include $^{125}$I, $^{123}$I, $^{99}$Tc, $^{43}$K, $^{52}$Fe, $^{67}$Ga, $^{68}$Ga, as well as $^{111}$In. Antibodies have also been labeled with a variety of radionuclides for potential use in targeted immunotherapy Peirersz et al. *Immunol. Cell Biol.* 65: 111-125 (1987). These radionuclides include $^{188}$Re and $^{186}$Re as well as $^{199}$Au and $^{67}$Cu to a lesser extent. U.S. Pat. No. 5,460,785 provides additional data regarding such radioisotopes and is incorporated herein by reference.

In addition to radionuclides, the dimeric antibodies of the present invention may be conjugated to, or associated with, any one of a number of biological response modifiers, pharmaceutical agents, toxins or immunologically active ligands. Those skilled in the art will appreciate that these non-radioactive conjugates may be assembled using a variety of techniques depending on the selected cytotoxin. For example, conjugates with biotin are prepared e.g. by reacting the dimeric antibodies with an activated ester of biotin such as the biotin N-hydroxysuccinimide ester. Similarly, conjugates with a fluorescent marker may be prepared in the presence of a coupling agent, e.g. those listed above, or by reaction with an isothiocyanate, preferably fluorescein-isothiocyanate. Conjugates of the tetravalent antibodies of the invention with cytostatic/cytotoxic substances and metal chelates are prepared in an analogous manner.

Preferred agents for use in the present invention are cytotoxic drugs, particularly those which are used for cancer therapy. Such drugs include, in general, cytostatic agents, alkylating agents, antimetabolites, anti-proliferative agents, tubulin binding agents, hormones and hormone antagonists, and the like. Exemplary cytostatics that are compatible with the present invention include alkylating substances, such as mechlorethamine, triethylenephosphoramide, cyclophosphamide, ifosfamide, chlorambucil, busulfan, melphalan or triaziquone, also nitrosourea compounds, such as carmustine, lomustine, or semustine. Other preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, carminomycin, daunorubicin (daunomycin), doxorubicin, aminopterin, methotrexate, methopterin, mithramycin, streptonigrin, dichloromethotrexate, mitomycin C, actinomycin-D, porfiromycin, 5-fluorouracil, floxuridine, ftorafur, 6-mercaptopurine, cytarabine, cytosine arabinoside, podophyllotoxin, or podophyllotoxin derivatives such as etoposide or etoposide phosphate, melphalan, vinblastine, vincristine, leurosidine, vindesine, leurosine and the like. Still other cytotoxins that are compatible with the teachings herein include taxol, taxane, cytochalasin B, gramicidin D, ethidium bromide, emetine, tenoposide, colchicin, dihydroxy anthracin dione, mitoxantrone, procaine, tetracaine, lidocaine, propranolol, and puromycin and analogs or homologs thereof. Hormones and hormone antagonists, such as corticosteroids, e.g. prednisone, progestins, e.g. hydroxyprogesterone or medroprogesterone, estrogens, e.g. diethylstilbestrol, antiestrogens, e.g. tamoxifen, androgens, e.g. testosterone, and aromatase inhibitors, e.g. aminogluthetimide are also compatible with the teachings herein. As noted previously, one skilled in the art may make chemical modifications to the desired compound in order to make reactions of that compound more convenient for purposes of preparing conjugates of the invention.

One example of particularly preferred cytotoxins comprise members or derivatives of the enediyne family of anti-tumor antibiotics, including calicheamicin, esperamicins or dynemicins. These toxins are extremely potent and act by cleaving nuclear DNA, leading to cell death. Unlike protein toxins which can be cleaved in vivo to give many inactive but immunogenic polypeptide fragments, toxins such as calicheamicin, esperamicins and other enediynes are small molecules which are essentially non-immunogenic. These non-peptide toxins are chemically-linked to the dimers or tetramers by techniques which have been previously used to label monoclonal antibodies and other molecules. These linking technologies include site-specific linkage via the N-linked sugar residues present only on the Fc portion of the constructs. Such site-directed linking methods have the advantage of reducing the possible effects of linkage on the binding properties of the constructs.

As previously alluded to, compatible cytotoxins may comprise a prodrug. As used herein, the term "prodrug" refers to a precursor or derivative form of a pharmaceutically active substance that is less cytotoxic to tumor cells compared to the parent drug and is capable of being enzymatically activated or converted into the more active parent form. Prodrugs compatible with the invention include, but are not limited to, phosphate-containing prodrugs, thiophosphate-containing prodrugs, sulfate containing prodrugs, peptide containing prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs that can be converted to the more active cytotoxic free drug. Further examples of cytotoxic drugs that can be derivatized into a prodrug form for use in the present invention comprise those chemotherapeutic agents described above.

Among other cytotoxins, it will be appreciated that dimeric antibodies can also be associated with a biotoxin such as ricin subunit A, abrin, diptheria toxin, botulinum, cyanginosins, saxitoxin, shigatoxin, tetanus, tetrodotoxin, trichothecene, verrucologen or a toxic enzyme. Preferably, such constructs will be made using genetic engineering techniques that allow for direct expression of the antibody-toxin construct. Other biological response modifiers that may be associated with the modified antibodies of the present invention comprise cytokines such as lymphokines and interferons. In view of the instant disclosure it is submitted that one skilled in the art could readily form such constructs using conventional techniques.

Another class of compatible cytotoxins that may be used in conjunction with the disclosed tetravalent antibodies are radiosensitizing drugs that may be effectively directed to tumor or immunoreactive cells. Such drugs enhance the sensitivity to ionizing radiation, thereby increasing the efficacy of radiotherapy. An antibody conjugate internalized by the tumor cell would deliver the radiosensitizer nearer the nucleus where radiosensitization would be maximal. The unbound radiosensitizer linked modified antibodies would be cleared quickly from the blood, localizing the remaining radiosensitization agent in the target tumor and providing minimal uptake in normal tissues. After rapid clearance from the blood, adjunct radiotherapy would be administered in one of three ways: 1.) external beam radiation directed specifically to the tumor, 2.) radioactivity directly implanted in the tumor or 3.) systemic radioimmunotherapy with the same targeting antibody. A potentially attractive variation of this approach would be the attachment of a therapeutic radioisotope to the radiosensitized immunoconjugate, thereby providing the convenience of administering to the patient a single drug.

Whether or not the disclosed tetravalent antibodies are used in a conjugated or unconjugated form, it will be appreciated that a major advantage of the present invention is the ability to use these dimeric constructs in myelosuppressed patients, especially those who are undergoing, or have undergone, adjunct therapies such as radiotherapy or chemotherapy. That is, the beneficial delivery profile (i.e. relatively short serum dwell time, high binding affinity and enhanced localization) of the dimeric antibodies makes them particularly useful for treating patients that have reduced red marrow reserves and are sensitive to myelotoxicity. In this regard, the unique delivery profile of the dimeric antibodies make them very effective for the administration of radiolabeled conjugates to myelosuppressed cancer patients. As such, the modified antibodies are useful in a conjugated or unconjugated form in patients that have previously undergone adjunct therapies such as external beam radiation or chemotherapy. In other preferred embodiments, the dimeric antibodies (again in a conjugated or unconjugated form) may be used in a combined therapeutic regimen with chemotherapeutic agents. Those skilled in the art will appreciate that such therapeutic regimens may comprise the sequential, simultaneous, concurrent or coextensive administration of the disclosed antibodies and one or more chemotherapeutic agents. Particularly preferred embodiments of this aspect of the invention will comprise the administration of a radiolabeled dimeric antibody.

While the dimeric antibodies may be administered as described immediately above, it must be emphasized that in other embodiments conjugated and unconjugated dimeric antibodies may be administered to otherwise healthy patients as a first line therapeutic agent. In such embodiments the dimeric antibodies may be administered to patients having normal or average red marrow reserves and/or to patients that have not, and are not, undergoing adjunct therapies such as external beam radiation or chemotherapy.

However, as discussed above, selected embodiments of the invention comprise the administration of dimeric antibodies to myelosuppressed patients or in combination or conjunction with one or more adjunct therapies such as radiotherapy or chemotherapy (i.e. a combined therapeutic regimen). As used herein, the administration of dimeric antibodies in conjunction or combination with an adjunct therapy means the sequential, simultaneous, coextensive, concurrent, concomitant or contemporaneous administration or application of the therapy and the disclosed antibodies. Those skilled in the art will appreciate that the administration or application of the various components of the combined therapeutic regimen may be timed to enhance the overall effectiveness of the treatment. For example, chemotherapeutic agents could be administered in standard, well known courses of treatment followed within a few weeks by radioimmunoconjugates of the present invention. Conversely, cytotoxin associated dimeric antibodies could be administered intravenously followed by tumor localized external beam radiation. In yet other embodiments, the dimeric antibody may be administered concurrently wit one or more selected chemotherapeutic agents in a single office visit. A skilled artisan (e.g. an experienced oncologist) would be readily be able to discern effective combined therapeutic regimens without undue experimentation based on the selected adjunct therapy and the teachings of the instant specification.

In this regard it will be appreciated that the combination of the dimeric antibody (with or without cytotoxin) and the chemotherapeutic agent may be administered in any order and within any time frame that provides a therapeutic benefit to the patient. That is, the chemotherapeutic agent and dimeric antibody may be administered in any order or concurrently. In selected embodiments the dimeric antibodies of the present invention will be administered to patients that have previously undergone chemotherapy. In yet other embodiments, the dimeric antibodies and the chemotherapeutic treatment will be administered substantially simultaneously or concurrently. For example, the patient may be given the modified antibody while undergoing a course of chemotherapy. In preferred embodiments the modified antibody will be administered within 1 year of any chemotherapeutic agent or treatment. In other preferred embodiments the dimeric antibody will be administered within 10, 8, 6, 4, or 2 months of any chemotherapeutic agent or treatment. In still other preferred embodiments the dimeric antibody will be administered within 4, 3, 2 or 1 week of any chemotherapeutic agent or treatment. In yet other embodiments the dimeric antibody will be administered within 5, 4, 3, 2 or 1 days of the selected chemotherapeutic agent or treatment. It will further be appreciated that the two agents or treatments may be administered to the patient within a matter of hours or minutes (i.e. substantially simultaneously).

Moreover, in accordance with the present invention a myelosuppressed patient shall be held to mean any patient exhibiting lowered blood counts. Those skilled in the art will appreciate that there are several blood count parameters conventionally used as clinical indicators of myelosuppression and one can easily measure the extent to which myelosuppresion is occurring in a patient. Examples of art accepted myelosuppression measurements are the Absolute Neutrophil Count (ANC) or platelet count. Such myelosuppression or partial myeloablation may be a result of various biochemical disorders or diseases or, more likely, as the result of prior chemotherapy or radiotherapy. In this respect, those skilled in the art will appreciate that patients who have undergone traditional chemotherapy typically exhibit reduced red marrow reserves. As discussed above, such subjects often cannot be treated using optimal levels of cytotoxin (i.e. radionuclides) due to unacceptable side effects such as anemia or immunosuppression that result in increased mortality or morbidity.

More specifically conjugated or unconjugated dimeric antibodies of the present invention may be used to effectively treat patients having ANCs lower than about 2000/$mm^3$ or platelet counts lower than about 150,000/$mm^3$. More preferably the dimeric antibodies of the present invention may be used to treat patients having ANCs of less than about 1500/$mm^3$, less than about 1000/$mm^3$ or even more preferably less than about 500/$mm^3$. Similarly, the dimeric antibodies of the present invention may be used to treat patients having a platelet count of less than about 75,000/$mm^3$, less than about 50,000/$mm^3$ or even less than about 10,000/$mm^3$. In a more general sense, those skilled in the art will easily be able to determine when a patient is myelosuppressed using government implemented guidelines and procedures.

As indicated above, many myelosuppressed patients have undergone courses of treatment including chemotherapy, implant radiotherapy or external beam radiotherapy. In the case of the latter, an external radiation source is for local irradiation of a malignancy. For radiotherapy implantation methods, radioactive reagents are surgically located within the malignancy, thereby selectively irradiating the site of the disease. In any event, the disclosed dimeric antibodies may be used to treat disorders in patients exhibiting myelosuppression regardless of the cause.

In this regard it will further be appreciated that the dimeric antibodies of the instant invention may be used in conjunction or combination with any chemotherapeutic agent or agents (e.g. to provide a combined therapeutic regimen) that eliminates, reduces, inhibits or controls the growth of neoplastic cells in vivo. As discussed, such agents often result in the reduction of red marrow reserves. This reduction may be offset, in whole or in part, by the diminished myelotoxicity of the compounds of the present invention that advantageously allow for the aggressive treatment of neoplasms in such patients. In other preferred embodiments the radiolabeled immunoconjugates disclosed herein may be effectively used with radiosensitizers that increase the susceptibility of the neoplastic cells to radionuclides. For example, radiosensitizing compounds may be administered after the radiolabeled modified antibody has been largely cleared from the bloodstream but still remains at therapeutically effective levels at the site of the tumor or tumors.

With respect to these aspects of the invention, exemplary chemotherapic agents that are compatible with the instant invention include alkylating agents, vinca alkaloids (e.g., vincristine and vinblastine), procarbazine, methotrexate and prednisone. The four-drug combination MOPP (mechlethamine (nitrogen mustard), vincristine (Oncovin), procarbazine and prednisone) is very effective in treating various types of lymphoma and comprises a preferred embodiment of the present invention. In MOPP-resistant patients, ABVD (e.g., adriamycin, bleomycin, vinblastine and dacarbazine), ChlVPP (chlorambucil, vinblastine, procarbazine and prednisone), CABS (lomustine, doxorubicin, bleomycin and streptozotocin), MOPP plus ABVD, MOPP plus ABV (doxorubicin, bleomycin and vinblastine) or BCVPP (carmustine, cyclophosphamide, vinblastine, procarbazine and prednisone) combinations can be used. Arnold S. Freedman and Lee M. Nadler, *Malignant Lymphomas*, in HARRISON'S PRINCIPLES OF INTERNAL MEDICINE 1774-1788 (Kurt J. Isselbacher et al., eds., $13^{th}$ ed. 1994) and V. T. DeVita et al., (1997) and the references cited therein for standard dosing and scheduling. These therapies can be used unchanged, or altered as needed for a particular patient, in combination with one or more modified antibodies as described herein.

Additional regimens that are useful in the context of the present invention include use of single alkylating agents such as cyclophosphamide or chlorambucil, or combinations such as CVP (cyclophosphamide, vincristine and prednisone), CHOP (CVP and doxorubicin), C-MOPP (cyclophosphamide, vincristine, prednisone and procarbazine), CAP-BOP (CHOP plus procarbazine and bleomycin), m-BACOD (CHOP plus methotrexate, bleomycin and leucovorin), ProMACE-MOPP (prednisone, methotrexate, doxorubicin, cyclophosphamide, etoposide and leucovorin plus standard MOPP), ProMACE-CytaBOM (prednisone, doxorubicin, cyclophosphamide, etoposide, cytarabine, bleomycin, vincristine, methotrexate and leucovorin) and MACOP-B (methotrexate, doxorubicin, cyclophosphamide, vincristine, fixed dose prednisone, bleomycin and leucovorin). Those skilled in the art will readily be able to determine standard dosages and scheduling for each of these regimens. CHOP has also been combined with bleomycin, methotrexate, procarbazine, nitrogen mustard, cytosine arabinoside and etoposide. Other compatible chemotherapeutic agents include, but are not limited to, 2-chlorodeoxyadenosine (2-CDA), 2'-deoxycoformycin and fludarabine.

For patients with intermediate- and high-grade NHL, who fail to achieve remission or relapse, salvage therapy is used. Salvage therapies employ drugs such as cytosine arabinoside, cisplatin, etoposide and ifosfamide given alone or in combination. In relapsed or aggressive forms of certain neoplastic disorders the following protocols are often used: IMVP-16 (ifosfamide, methotrexate and etoposide), MIME (methyl-gag, ifosfamide, methotrexate and etoposide), DHAP (dexamethasone, high dose cytarabine and cisplatin), ESHAP (etoposide, methylpredisolone, HD cytarabine, cisplatin), CEPP(B) (cyclophosphamide, etoposide, procarbazine, prednisone and bleomycin) and CAMP (lomustine, mitoxantrone, cytarabine and prednisone) each with well known dosing rates and schedules.

The amount of chemotherapeutic agent to be used in combination with the dimeric antibodies of the instant invention may vary by subject or may be administered according to what is known in the art. See for example, Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., $9^{th}$ ed. 1996).

As previously discussed, the tetravalent antibodies of the present invention, immunoreactive fragments or recombinants thereof may be administered in a pharmaceutically effective amount for the in vivo treatment of mammalian disorders. In this regard, it will be appreciated that the disclosed antibodies will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of the dimeric antibody, immunoreactive fragment or recombinant thereof, conjugated or unconjugated to a therapeutic agent, shall be held to mean an amount sufficient to achieve effective binding with selected immunoreactive antigens on neoplastic or immunoreactive cells and provide for an increase in the death of those cells. Of course, the pharmaceutical compositions of the present invention may be administered in single or multiple doses to provide for a pharmaceutically effective amount of the dimeric antibody.

More specifically, they the disclosed antibodies and methods should be useful for reducing tumor size, inhibiting tumor growth and/or prolonging the survival time of tumor-bearing animals. Accordingly, this invention also relates to a method of treating tumors in a human or other animal by administering to such human or animal an effective, non-toxic amount of dimeric antibody. One skilled in the art would be able, by routine experimentation, to determine what an effective, non-toxic amount of dimeric antibody would be for the purpose of treating malignancies. For example, a therapeutically active amount of a dimeric antibody may vary according to factors such as the disease stage (e.g., stage I versus stage IV), age, sex, medical complications (e.g., immunosuppressed conditions or diseases) and weight of the subject, and the ability of the antibody to elicit a desired response in the subject. The dosage regimen may be adjusted to provide the optimum therapeutic response. For example, several divided doses may be administered daily, or the dose may be proportionally reduced as indicated by the exigencies of the therapeutic situation. Generally, however, an effective dosage is expected to be in the range of about 0.05 to 100 milligrams per kilogram body weight per day and more preferably from about 0.5 to 10 milligrams per kilogram body weight per day.

For purposes of clarification "Mammal" refers to any animal classified as a mammal, including humans, domestic and farm animals, and zoo, sports, or pet animals, such as dogs, horses, cats, cows, etc. Preferably, the mammal is human.

"Treatment" refers to both therapeutic treatment and prophylactic or preventative measures. Those in need of treatment include those already with the disease or disorder as well as those in which the disease or disorder is to be prevented. Hence, the mammal may have been diagnosed as having the disease or disorder or may be predisposed or susceptible to the disease.

In keeping with the scope of the present disclosure, the dimeric antibodies of the invention may be administered to a human or other animal in accordance with the aforementioned methods of treatment in an amount sufficient to produce such effect to a therapeutic or prophylactic degree. The antibodies of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of dimeric antibodies according to the present invention may prove to be particularly effective.

Methods of preparing and administering conjugates of the antibody, immunoreactive fragments or recombinants thereof, and a therapeutic agent are well known to or readily determined by those skilled in the art. The route of administration of the dimeric antibody (or fragment thereof) of the invention may be oral, parenteral, by inhalation or topical. The term parenteral as used herein includes intravenous, intraarterial, intraperitoneal, intramuscular, subcutaneous, rectal or vaginal administration. The intravenous, intraarterial, subcutaneous and intramuscular forms of parenteral administration are generally preferred. While all these forms of administration are clearly contemplated as being within the scope of the invention, a preferred administration form would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumine), etc. However, in other methods compatible with the teachings herein, the dimeric antibodies can be delivered directly to the site of the adverse cellular population thereby increasing the exposure of the diseased tissue to the therapeutic agent.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a dimeric antibody by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 and U.S. Ser. No. 09/259,338, now abandoned, each of which is incorporated herein by reference. Such articles of manufacture will preferably have labels or package inserts indicating that the associated compositions are useful for treating a subject suffering from, or predisposed to autoimmune or neoplastic disorders.

As discussed in detail above, preferred embodiments of the present invention provide compounds, compositions, kits and methods for the treatment of neoplastic disorders in a mammalian subject in need of treatment thereof. Preferably, the subject is a human. The neoplastic disorder (e.g., cancers and malignancies) may comprise solid tumors such as melanomas, gliomas, sarcomas, and carcinomas as well as myeloid or hematologic malignancies such as lymphomas and leukemias. In general, the disclosed invention may be used to prophylactically or therapeutically treat any neoplasm comprising an antigenic marker that allows for the targeting of the cancerous cells by the modified antibody. Exemplary cancers that may be treated include, but are not limited to, prostate, gastric carcinomas such as colon, skin, breast, ovarian, lung and pancreatic. More particularly, the antibodies of the instant invention may be used to treat Kaposi's sarcoma. CNS neoplasms (capillary hemangioblastomas, meningiomas and cerebral metastases), melanoma, gastrointestinal and renal sarcomas, rhabdomyosarcoma, glioblastoma (preferably glioblastoma multiforme), leiomyosarcoma, retinoblastoma, papillary cystadenocarcinoma of the overy, Wilm's tumor or small cell lung carcinoma. It will be appreciated that appropriate dimeric antibodies may be derived for tumor associated antigens related to each of the forgoing neoplasms without undue experimentation in view of the instant disclosure.

Exemplary hematologic malignancies that are amenable to treatment with the disclosed invention include Hodgkins and non-Hodgkins lymphoma as well as leukemias, including ALL-L3 (Burkitt's type leukemia), chronic lymphocytic leukemia (CLL) and monocytic cell leukemias. It will be appreciated that the compounds and methods of the present invention are particularly effective in treating a variety of B-cell lymphomas, including low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL and Waldenstrom's Macroglobulinemia. It should be clear to those of skill in the art that these lymphomas will often have different names due to changing systems of classification, and that patients having lymphomas classified under different names may also benefit from the combined therapeutic regimens of the present invention. In addition to the aforementioned neoplastic disorders, it will be appreciated that the disclosed invention may advantageously be used to treat additional malignancies bearing compatible tumor associated antigens.

Besides neoplastic disorders, the dimeric antibodies of the instant invention are particularly effective in the treatment of autoimmune disorders or abnormal immune responses. In this regard, it will be appreciated that both homodimers and heterodimers may be used to control, suppress, modulate or eliminate unwanted immune responses to both external and autoantigens. For example, in one embodiment, the antigen is an autoantigen. In another embodiment, the antigen is an allergan. In yet other embodiments, the antigen is an alloantigen or xenoantigen. Use of the disclosed tetravalent antibodies to reduce an immune response to alloantigens and xenoantigens is of particular use in transplantation, for example to inhibit rejection by a transplant recipient of a donor graft, e.g. a tissue or organ graft or bone marrow transplant. Additionally, suppression or elimination of donor T cells within a bone marrow graft is useful for inhibiting graft versus host disease.

In yet other embodiments the dimeric antibodies of the present invention may be used to treat immune disorders that include, but are not limited to, allergic bronchopulmonary aspergillosis; Allergic rhinitis Autoimmune hemolytic anemia; Acanthosis nigricans; Allergic contact dermatitis; Addison's disease; Atopic dermatitis; Alopecia areata; Alopecia universalis; Amyloidosis; Anaphylactoid purpura; Anaphylactoid reaction; Aplastic anemia; Angioedema, hereditary; Angioedema, idiopathic; Ankylosing spondylitis; Arteritis, cranial; Arteritis, giant cell; Arteritis, Takayasu's; Arteritis, temporal; Asthma; Ataxia-telangicetasia; Autoimmune oophoritis; Autoimmune orchitis; Autoimmune polyendocrine failure; Behcet's disease; Berger's disease; Buerger's disease; bronchitis; Bullous pemphigus; Candidiasis, chronic mucocutaneous; Caplan's syndrome; Post-myocardial infarction syndrome; Post-pericardiotomy syndrome; Carditis; Celiac sprue; Chagas's disease; Chediak-Higashi syndrome; Churg-Strauss disease; Cogan's syndrome; Cold agglutinin disease; CREST syndrome; Crohn's disease; Cryoglobulinemia; Cryptogenic fibrosing alveolitis; Dermatitis herpetifomis; Dermatomyositis; Diabetes mellitus; Diamond-Blackfan syndrome; DiGeorge syndrome; Discoid lupus erythematosus; Eosinophilic fasciitis; Episcleritis; Drythema elevatum diutinum; Erythema marginatum; Erythema multiforme; Erythema nodosum; Familial Mediterranean fever; Felty's syndrome; Fibrosis pulmonary; Glomerulonephritis, anaphylactoid; Glomerulonephritis, autoimmune; Glomerulonephritis, post-streptococcal; Glomerulonephritis, post-transplantation; Glomerulopathy, membranous; Goodpasture's syndrome; Granulocytopenia, immune-mediated; Granuloma annulare; Granulomatosis, allergic; Granulomatous myositis; Grave's disease; Hashimoto's thyroiditis; Hemolytic disease of the newborn; Hemochromatosis, idiopathic; Henoch-Schoenlein purpura; Hepatitis, chronic active and chronic progressive; Histiocytosis X; Hypereosinophilic syndrome; Idiopathic thrombocytopenic purpura; Job's syndrome; Juvenile dermatomyositis; Juvenile rheumatoid arthritis (Juvenile chronic arthritis); Kawasaki's disease; Keratitis; Keratoconjunctivitis sicca; Landry-Guillain-Barre-Strohl syndrome; Leprosy, lepromatous; Loeffler's syndrome; lupus; Lyell's syndrome; Lyme disease; Lymphomatoid granulomatosis; Mastocytosis, systemic; Mixed connective tissue disease; Mononeuritis multiplex; Muckle-Wells syndrome; Mucocutaneous lymph node syndrome; Mucocutaneous lymph node syndrome; Multicentric reticulohistiocytosis; Multiple sclerosis; Myasthenia gravis; Mycosis fungoides; Necrotizing vasculitis, systemic; Nephrotic syndrome; Overlap syndrome; Panniculitis; Paroxysmal cold hemoglobinuria; Paroxysmal nocturnal hemoglobinuria; Pemphigoid; Pemphigus; Pemphigus erythematosus; Pemphigus foliaceus; Pemphigus vulgaris; Pigeon breeder's disease; Pneumonitis, hypersensitivity; Polyarteritis nodosa; Polymyalgia rheumatic; Polymyositis; Polyneuritis, idiopathic; Portuguese familial polyneuropathies; Pre-eclampsia/eclampsia; Primary biliary cirrhosis; Progressive systemic sclerosis (Scleroderma); Psoriasis; Psoriatic arthritis; Pulonary alveolar proteinosis; Pulmonary fibrosis, Raynaud's phenomenon/syndrome; Reidel's thyroiditis; Reiter's syndrome, Relapsing polychrondritis; Rheumatic fever; Rheumatoid arthritis; Sarcoidosis; Scleritis; Sclerosing cholangitis; Serum sickness; Sezary syndrome; Sjogren's syndrome; Stevens-Johnson syndrome; Still's disease; Subacute sclerosing panencephalitis; Sympathetic ophthalmia; Systemic lupus erythematosus; Transplant rejection; Ulcerative colitis; Undifferentiated connective tissue disease; Urticaria, chronic; Urticaria, cold; Uveitis; Vitiligo; Weber-Christian disease; Wegener's granulomatosis and Wiskott-Aldrich syndrome.

The foregoing description will be more fully understood with reference to the following examples. Such examples, are, however, demonstrative of preferred methods of practicing the present invention and are not limiting of the scope of the invention or the claims appended hereto.

EXAMPLE 1

Construction and Expression of a C2B8.$\Delta C_H2$ Immunoglobulin

The chimeric antibody C2B8 (IDEC Pharmaceuticals) was modified to create a domain deleted version lacking the $C_H2$ domain within the human gamma 1 constant region. C2B8 and the plasmid N5KG1, which is an "empty" vector encodes a human kappa light chain constant region as well as a human gamma 1 constant region, are described in U.S. Pat. Nos. 5,648,267 and 5,736,137 each of which is incorporated herein by reference. Creation of a $C_H2$ domain deleted version was accomplished by way of overlapping PCR mutagenesis.

The gamma 1 constant domain begins with a plasmid encoded Nhe I site with is in translational reading frame with the immunoglobulin sequence. A 5' PCR primer was constructed encoding the Nhe I site as well as sequence immediately downstream. A 3' PCR primer mate was constructed such that it anneals with the 3' end of the immunoglobulin hinge region and encodes in frame the first several amino acid of the gamma 1 CH3 domain. A second PCR primer pair consisted of the reverse complement of the 3' PCR primer from the first pair (above) as the 5' primer and a 3' primer that anneals at a loci spanning the BsrG 1 restriction site within the $C_H3$ domain. Following each PCR amplification, the resultant products were utilized as template with the Nhe I and BsrG I 5' and 3', respectively primers. The amplified product was then cloned back into N5KG1 to create the plasmid N5KG1$\Delta C_H2$. This construction places the intact CH3 domain immediately downstream and in frame with the intact hinge region. As this is an "empty" vector, the C2B8 immunoglobulin light and heavy chain variable domains were then inserted in the appropriate cloning sites.

Following sequence confirmation of the immunoglobulin coding regions, this expression construct was transfected into CHO DG44 cells and selected for G418 resistance (conferred by a vector encoded neomycin phosphotransferase gene). Resistant cell isolates were then assayed for C2B8.$\Delta C_H2$ immunoglobulin expression. The nucleotide sequences encoding the light and heavy chains of C2B8.$\Delta C_H2$ immunoglobulin in the resulting construct are shown in FIGS. 2B and 3A (SEQ ID NOs: 4 and 5).

EXAMPLE 2

Construction and Expression of a huCC49.$\Delta C_H2$ Immunoglobulin

A humanized version of the CC49 antibody (ATCC No. HB 9459) was obtained from the National Cancer Institute. The light chain was encoded in a plasmid referred to as pLNCX II HuCC49 HuK. The Heavy Chain was encoded in a plasmid referred to as pLgpCX II HuCC49G1.$\Delta C_H2$.

The light and heavy chain variable domains only were isolated from these plasmids by PCR amplification. PCR primers were constructed such that restriction endonuclease sites were included allowing subsequent subcloning into IDEC's proprietary expression vector N5KG1.$\Delta C_H2$.

The light chain restriction enzymes were Bgl II at the 5' end (immediately upstream of the translation initiation codon for the natural leader peptide encoded by the NCI plasmid) and BsiW I at the 3' end (in translational reading frame with IDEC's vector encoded human kappa light chain constant domain. No amino acids within the light chain variable domain were changed from the NCI sequence.

The heavy chain restriction enzymes were Mlu I at the 5' end (encoding in frame amino acid residues −5 and −4 of the "synthetic" immunoglobulin heavy chain signal peptide encode by IDEC's expression vector). The PCR primer also encoded residues −3, −2 and −1 with respect to the beginning of the heavy variable domain. The 3' heavy chain PCR primer encoded the restriction enzyme Nhe I which codes in frame with IDEC's gamma 1 domain deleted heavy chain constant region. The final result is an expression construct encoding the HuCC49 domain deleted antibody with the following components. No amino acids within the heavy chain variable domain were changed from the NCI sequence.

Light chain: Natural light chain leader-NCI variable domain-IDEC's human kappa constant domain.

Heavy chain: IDEC's synthetic heavy leader-NCI variable domain-IDEC's CH2 domain deleted gamma 1 heavy chain constant domain.

Following sequence confirmation of the immunoglobulin coding regions, this expression construct was transfected into CHO DG44 cells and selected for G418 resistance (conferred by a vector encoded neomycin phosphotransferase gene). Resistant cell isolates were then assayed for HuCC49.$\Delta C_H2$ immunoglobulin expression. The nucleotide sequences for the HuCC49.$\Delta C_H2$ light and heavy chains are shown in FIGS. 4B and 5B (SEQ ID NOs: 8 and 10).

EXAMPLE 3

Construction and Expression of a C5E10.$\Delta C_H2$ Immunoglobulin

Murine C5E10 expressing hybridoma cells were received from the University of Iowa. RNA from the cells and then made cDNA using oligo dT from the RNA. The cDNA was PCR amplified using a series of mouse kappa and heavy chain variable region primers. The PCR products were run on agarose gels. Using known techniques, primers were used to isolate and identify the light and heavy chain as bands in the agarose. The bands were isolated, cut with restriction enzymes and the light chain variable region was cloned into Neospla N5KG1 vector substantially as described in Examples 1 and 2. The heavy chain variable regions were then cloned into a Neospla $\Delta C_H2$ vector (also substantially as described in Examples 1 and 2) in order to generate an antibody missing the $C_H2$ domain. The DNA and amino acid sequences of the heavy and light chain variable regions of the parent antibody and the domain deleted construct were sequenced as shown in FIGS. 6 to 8. The vectors were electroporated into CHO cells using art known techniques to provide for stable cell line development. Following growth of the CHO cells and expression of the product, the modified antibodies were purified using affinity chromatography.

EXAMPLE 4

Purification of Tetravalent CC49.$\Delta C_H2$ Constructs

A composition comprising a mixture of monomeric ($H_2L_2$) and dimeric ($H_4L_4$) CC49.$\Delta C_H2$ antibodies produced as set forth in Example 2 was purified over a 2.4 mL Protein G column (Poros 20G, PerSeptive Biosystems). One liter of cell culture expression supernatant, pH adjusted to 7.5, was loaded onto the column at 0.5 mL per minute, 4° C. After washing the column with 50 mM Tris, pH 7.5, the domain deleted material was eluted with 0.1M Glycine, pH 3. One mL fractions containing 25 mM Tris, pH 9 for neutralization, were collected at a flow rate of 2 mL per minute. Fractions were monitored by A280 for protein content, pooled, dialyzed against PBS and analyzed by SDS-PAGE for purity and migration characteristics.

The Protein G-purified domain deleted constructs were analyzed for the presence of monomeric and dimeric forms of the antibody by size exclusion using an HPLC gel filtration column (HPLC-SEC), 50 to 100 uL of the collected fractions containing 100 ug of protein were injected into a Bio-Sil SEC 250 column (Bio-Rad, 7.8 mm×30 cm). Runs were 15 minutes, at a flow rate of 1 mL per minute in the following buffer: 50 mM NaH$_2$PO$_4$, 50 mM Na$_2$HPO$_4$, 150 mM NaCl, 10 mM NaN$_3$, pH 6.8.

FIG. 9 is an HPLC-SEC chromatograph showing the separate elution of the monomeric and dimeric forms of the antibody. As a control, a domain deleted CC49 construct that comprises an amino acid spacer (gly/ser spacer) and does not form a dimer was run under the same conditions. With the antibody mixture two distinct peaks were found representing molecular weights equivalent to 120 and 240 kDa. This chromatograph is representative of the migration profiles for domain deleted constructs that do not have a spacer molecule between the hinge and the C$_H$3 domain. In contrast, the antibody construct comprising a spacer CC49(gly/ser) that retards dimerization migrates as a single peak of 120 kDa that is similar to the migration profile of purified IgG.

EXAMPLE 5

PAGE Analysis of ΔC$_H$2 Constructs

Purified domain deleted constructs were further analyzed by SDS gel electrophoresis after 5 min incubation at 100° C. without a reducing agent. Such conditions will disrupt non-covalent associations between the antibody chains but leaves intact chains that are covalently linked. More specifically, test samples comprising 1-10 ug of protein are incubated with a Tris-Glycine buffer containing SDS.

Samples are added to wells of a commercially prepared polyacrylamide slab gel to which an electric field is applied. Typically, a constant voltage of 125 V for 90 minutes is sufficient to complete migration of the denatured species resulting from this procedure. Analysis follows with comparison to molecular weight standards run under the same denaturing conditions.

Under denaturing non-reducing conditions, gels comprising purified fractions of CC49.ΔC$_H$2 derived substantially as set forth in Example 4 show two molecular forms of the antibody are present. More particularly, by displaying bands at 120 kDa and 60 kDa the gels clearly show that the products purified from cell culture supernatant using Protein G contain a mixture of covalently and non-covalently linked heavy and light chains (lanes A-C). As discussed above these Protein G purified domain deleted MAb shown in FIG. 3, could be further purified using HPLC-SEC into homogenous (>98%) of 120 kDa or 240 kDa MAb fractions. The HPLC-SEC purified 240 kDa MAb fraction is shown in lane D while the 120 kDa MAb fraction is shown in lane E.

In this regard, Lane D shows a single band at 120 kDa that represents a domain deleted construct. The non-covalent attachments between the C$_H$3 domains of the two monomers that used to provide the H$_4$L$_4$ construct have been disrupted by the heating and detergent to release the antibodies which run concurrently in the gel. Conversely, lane E shows a single band at 60 kDa that represents a single heavy and light chain joined by a disulfide bond. Here, the non-covalent bond between the two C$_H$3 domains of the purified monomer has been disrupted to free the individual heavy and light chain combinations. As was discussed above, it is likely that the non-covalent interactions between the C$_H$3 domains in the monomer prevented the formation of disulfide bonds in the hinge region. Thus, when disrupted the construct released the single heavy and light chain still connected by a disulfide bond. Lane F demonstrates that the CC49 domain deleted construct having a Gly/Ser spacer comprises a mixture of the antibody variants.

EXAMPLE 6

Preparation of $^{111}$In and Eu Radiolabeled Constructs

Modified antibody constructs including dimers and appropriate controls were labeled with Europium and indium for in vitro binding determination and in vivo biodistribution and bioavailability studies as described below. As discussed above, direct incorporation of metals such as Eu or $^{111}$In to proteins is not generally effective. As such, chelators (e.g. bifunctional chelators) are typically used to link these isotopes to the antibody to provide the desired radioactive imunoconjugate. For the studies described herein a cyclohexal-DTPA (CHx-DTPA) chelator was used to associate the Eu or $^{111}$In with the dimeric antibodies.

MAb's CC49 (Gly/Ser spacer) and CC49.ΔC$_H$2 monomer and dimer were diafiltered into low metal containing saline (LMC-Saline, pH adjusted to 8.6 using 0.5M Boric acid) before conjugation. The MAb constructs were diafiltered using pre-washed Centricon 30 filters (two times, according to manufactures instruction), MAb concentration measured by A280 (1 mg/ml=1.0 AU) and diluted using LMC-Saline (pH 8.6) to approximately 10.0 mg/ml. The selected MAb was reacted with MX-DTPA at a 2:1 molar ratio (chelate to MAb) for 14-16 hours at room temperature. After incubation, the conjugate was clarified from unreacted chelate using Centricon 30 filters (3 times), protein concentration determined by A280 and adjusted to a final concentration of 2.0 mg/ml using LMC-Saline.

Following conjugation, the domain deleted constructs and control antibodies were radiolabeled with $^{111}$In. The $^{111}$In was labeled at specific activities ranging from 1 to 3 mCi/mg protein. Indium-[111]chloride in dilute HCl (Nycomed Amersham or Cyclotron Products Inc.) was adjusted to pH 4 using 50 mM sodium acetate. Immunoglobulin conjugate was added and the mixture incubated at ambient temperature. After 30 minutes, the mixture was diluted to a final antibody concentration of 0.2 mg/mL using 1XPBS, pH 7.2 containing 7.5% human serum albumin (HAS) and 1 mM diethylenetriaminepentaacetic acid (DTPA) (formulation buffer).

A commercially available kit (Delfia® Eu-Labelling Kit, Wallac Instruments, Gaithersburg, Md.) was used to label the CC49.ΔC$_H$2 constructs with Europium. In this regard the samples were labeled with Eu according to package instructions that came with the Eu labeling kit (Part #1244-302, lot #: 710715) to provide the desired specific activities.

EXAMPLE 7

Antigen Binding Activities of Monomeric and Dimeric CC49.ΔC$_H$2 Constructs

Figure 11A:
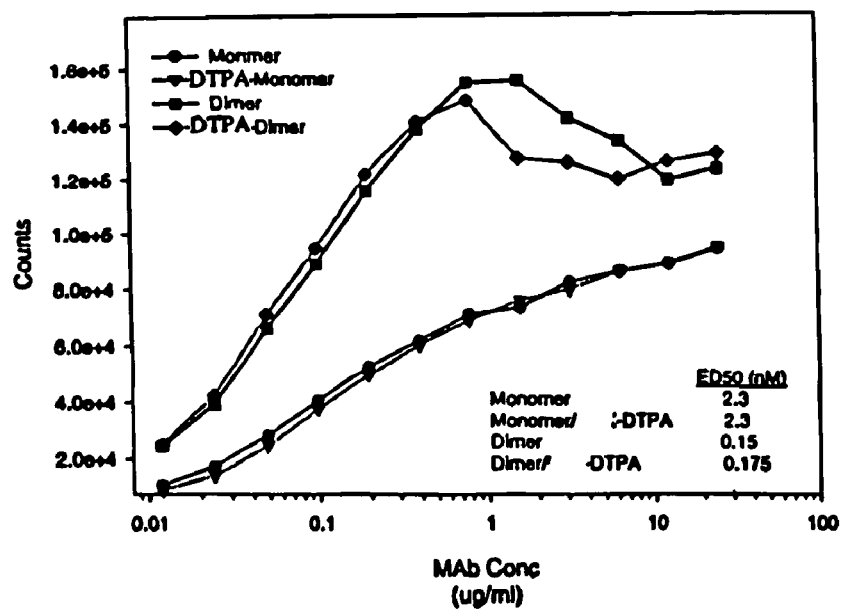
FIGS. 11A and 11B are graphical representations illustrating the antigen binding activity of the dimeric constructs of the present invention both before and after conjugation to DTPA as determined by ELISA assays on TAG-72 coated plates.

Antigen binding activity of the purified CC49.ΔC$_H$2 variants both before and after conjugation to DTPA was determined by ELISA assay on TAG-72 coated plates (FIG. 11A). The ELISAs were run as follows:
I. Prepare ELISA plate with BSM
 1. Prepare a 20 μg/mL solution of BSM in normal saline.
 2. Add 100 μL per well of the BSM at 20 μg/mL (Note: Total of 2 μg/well)
 3. Place plate or plates at 37° C. and allow to dry overnight.
II. Blocking of Plate
 1. Washed plate 3× with 0.025% Tween 20 in PBS
 2. Added 200 μL of Dilution Buffer (1% BSA in PBS, pH=7.4)
 3. Incubated the plate or plates at 37° C. for 60 minutes, or overnight at 2-8° C.

III. Binding Assay: Each Test Sample Was Performed in Triplicate
1. Following incubation washed plate 3× with 0.025% Tween 20 in PBS
2. Diluted the test antibodies to 0.025 mg/mL in Dilution Buffer
3. Performed the serial dilutions on a separate plate
4. From 0.025 mg/mL serially diluted the antibody 10×.
5. Added 100 µL of the diluted antibody to the blocked plate in triplicate.
6. Allowed the antibody to incubate for 3 hours at 37° C.
7. Washed the plate 3× with 0.025% Tween 20 in PBS
8. Diluted the Eu-F(ab')$_2$ Ms Anti Hu IgG to 0.1 µg/mL
9. Added 100 µL of Eu-F(ab')$_2$ Mu-anti Hu IgG at 0.1 µg/mL, to each well
10. Incubated the plate for 60 minutes at 37° C.
11. Washed the plate 3× with 0.025% Tween 20 in PBS
12. Added 200 µL of Perkin Elmer/Wallach's Enhancement Solution
13. Allowed plate to shake for 30 minutes at room temperature
14. Read plate in the Perkin Elmer/Wallach ELISA reader on the Eu setting
15. Determined the m3 value from a 4-parameter plot As shown in FIG. 11A antigen binding of purified monomeric (H$_2$L$_2$) or dimeric (H$_4$L$_4$) CC49.ΔC$_H$2 variants was unaffected by conjugation to CHx-DTPA, showing similar binding curves compared to the non-conjugated variant. However dimeric ddCC49 (H$_4$L$_4$) demonstrated much higher binding activity than its monomeric variant. Estimated kD was 2.3 nM for monomeric ddCC49, which is consistent with previous estimates of affinity using ddCC49 (Gly/Ser) or huCC49.IgG. The dimeric ddCC49 variant (H$_4$L$_4$) had a estimated kD on the order of 0.15 nM.

Figure 11B:
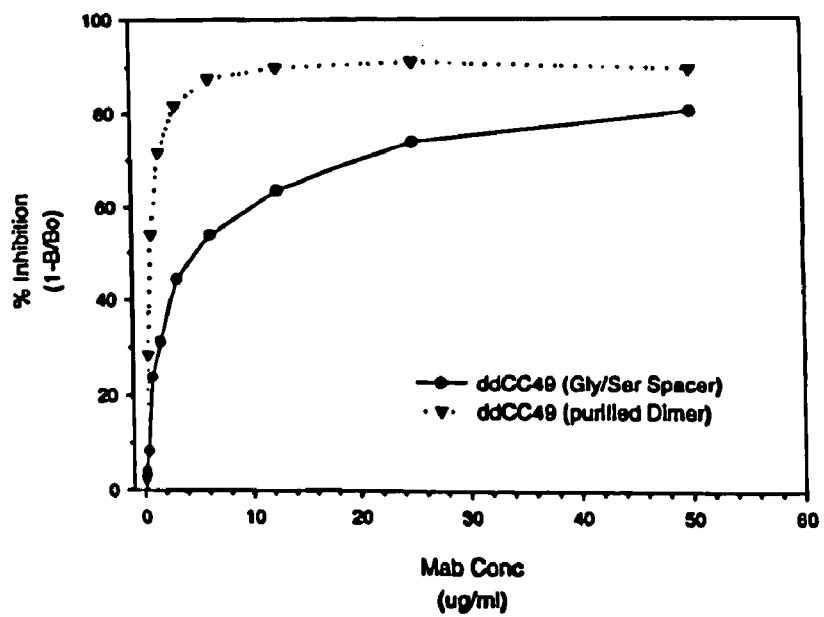

To insure that the increased binding activity associated with the dimerized variant of ddCC49 form was not due to differences in non-specific binding of a larger molecules, a competition biding assay using Europium labeled ddCC49 (Gly/Ser) binding to TAG-72 plates was done substantially as set forth above. The results are shown in FIG. 11B which clearly illustrates that the dimeric form of CC49.ΔC$_H$2 competes more effectively against Europium labeled ddCC49(Gly/Ser) than did unconjugated ddCC49(Gly/Ser).

EXAMPLE 8

Biodistribution of Radiolabeled huCC49.ΔC$_H$2 in Tumor Bearing Mice

In vivo assays were run to determine the biodistribution of the constructs of the present invention. More specifically, assays were run to determine the biodistribution of $^{111}$In labeled CC49.ΔC$_H$2-CHx-DTPA monomeric and dimeric constructs in nude mice exhibiting LS174T tumors. The purified radiolabeled monomers and dimers, obtained as set forth in the previous examples, were radiolabeled substantially as set forth in Example compared against radiolabeled CC49.ΔC$_H$2 (Gly/Ser) spacer.

Nude mice were injected subcutaneously with approximately 2×10$^6$ LS174T tumor cells (TAG 72 positive) to provide human tumor xenografts. One week after injection the mice were examined and sorted into groups of mice having palpable tumors of 100 250 mm$^3$. Each group consisted of 4 mice that were ear-marked for identification purposes.

One day after marking and sorting the mice were given one injection (i.v.) of in the tail vein with 10 µCi/0.1 mL of $^{111}$In labeled constructs (200 µg antibody/mouse in 200 µl) in PBS, and sacrificed at 5, 24 and 48 hours post injection. Each mouse was dissected to provide tissue samples for blood, spleen, liver, kidneys, heart, lungs, G.I. tract, muscle, femur and tumor. The organs were weighed and then counted on a gamma counter. From these measurements the %ID/gm tissue of the injected radiolabeled antibodies in tumors and normal tissue was determined. Additionally, 200 ul of blood was collected from each animal and counted directly before sacrifice to compare plasma clearance rates between the various constructs. All of the domain-deleted constructs (H$_2$L$_2$, H$_4$L$_4$ and gly/ser spacer) were cleared rapidly from the blood with <2% of the injected dose present in the blood at 24 hours post injection. In contrast, 24% of intact $^{111}$In labeled CC49 IgG was present in the blood 48 hours post injection (data not shown).

Figure 12A:
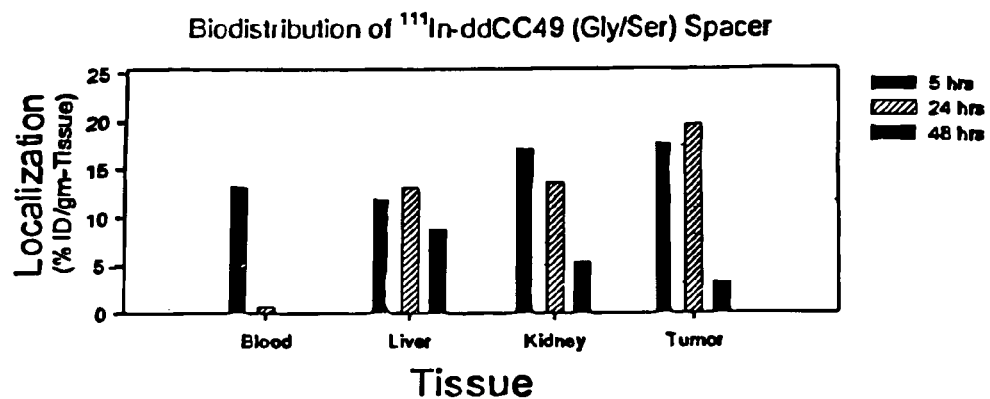
FIGS. 12A, 12B and 12C are, respectively, graphical representations of tissue and tumor localization rates of radiolabeled CC49.$\Delta C_H2$(gly/ser), the monomeric form of CC49.$\Delta C_H2$ and the dimeric form of CC49.$\Delta C_H2$ in LS174T murine xenograft models.
Figure 12B:
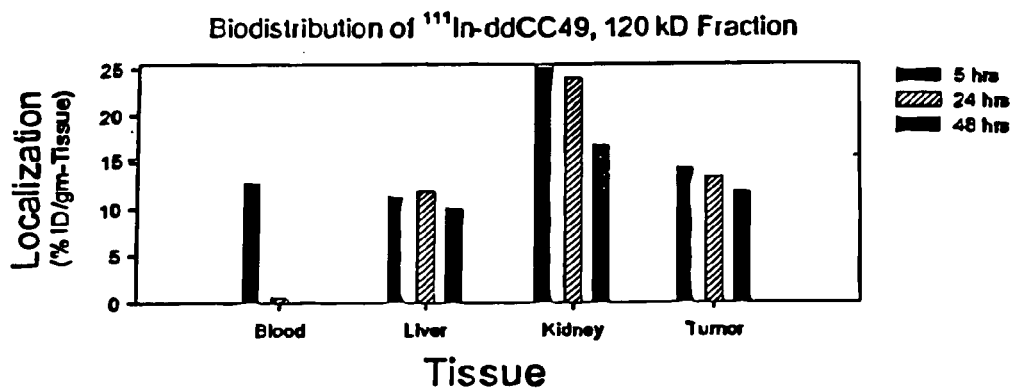
Figure 12C:
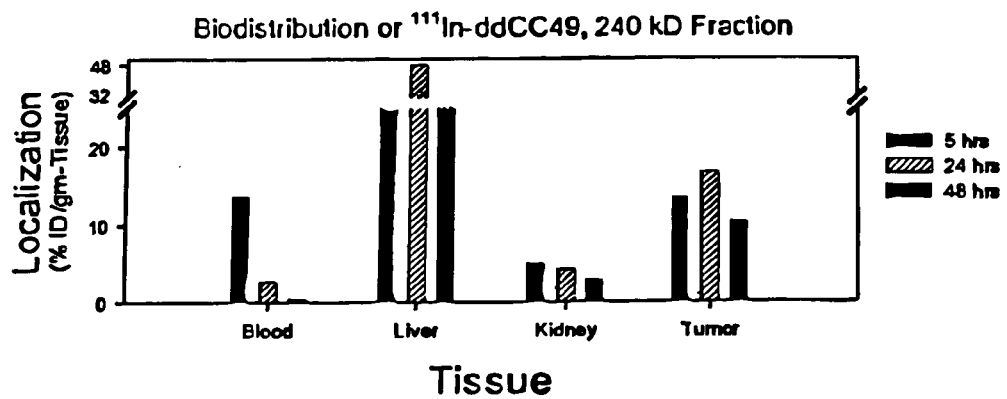

Tumor localization of $^{111}$In-labeled constructs is also shown in FIGS. 12A, 12B and 12C. All domain deleted variants, showed peak localization between 5-24 hours post injection of radiolabeled material. Peak localization (%ID/gm tissue) was similar for all the domain-deleted constructs at each time point tested. However, differences in the normal tissue biodistribution profile were observed between the dimeric (FIG. 12C) and monomeric (FIG. 12B) constructs. In particular, the purified CC49.ΔC$_H$2 dimer (240 kDa) showed increased accumulation of radioactive material in the liver and lower accumulation in the kidney than the other two constructs. The differences in the localization pattern of the dimer were observed at all time points tested. The purified monomer (120 kDa) showed similar accumulation of radioactive material in the liver when compared to the CC49.ΔC$_H$2 (Gly/Ser) (FIG. 12A) construct but a higher tumor localization at the last measured time point. The beneficial distribution profile of the dimer construct may be indicative of lower overall toxicity that could allow more efficacious doses of the radiolabeled antibodies to be administered.

EXAMPLE 9

Anti-tumor Activity of Dimeric C2B8.ΔC$_H$2 on Ramos Tumor Xenografts

In vivo assays were run to determine the anti-tumor activities of unlabeled dimeric constructs prepared according to the methods of the present invention. More specifically, assays were run to determine the anti-tumor activity of dimeric C2B8.ΔC$_H$2 (H$_4$L$_4$, 240 kDa) constructs in nude mice exhibiting tumor xenografts. The anti-tumor activity of the purified dimeric construct, obtained and purified substantially as set forth in the previous examples, was compared against the anti-CD20 antibody Rituxan® (IDEC Pharmaceuticals, San Diego, Calif.).

Nude mice were injected subcutaneously with approximately 20×10$^6$ Ramos tumor cells (CD20 positive) to provide human tumor xenografts. Two weeks after injection the mice were examined and sorted into groups of mice having palpable tumors of 100-150 mm$^3$. Each group consisted of 6 mice that were ear-marked for identification purposes. Following marking and sorting, the mice were given three injections forty eight hours apart (tail vein, i.v.) of Rituxan or the dimeric construct (200 µg antibody/mouse in 200 µl PBS). Tumor measurements were performed three times a week and the weight of the mice was measured twice a week. The results are graphically illustrated in FIG. 13.

Figure 13:
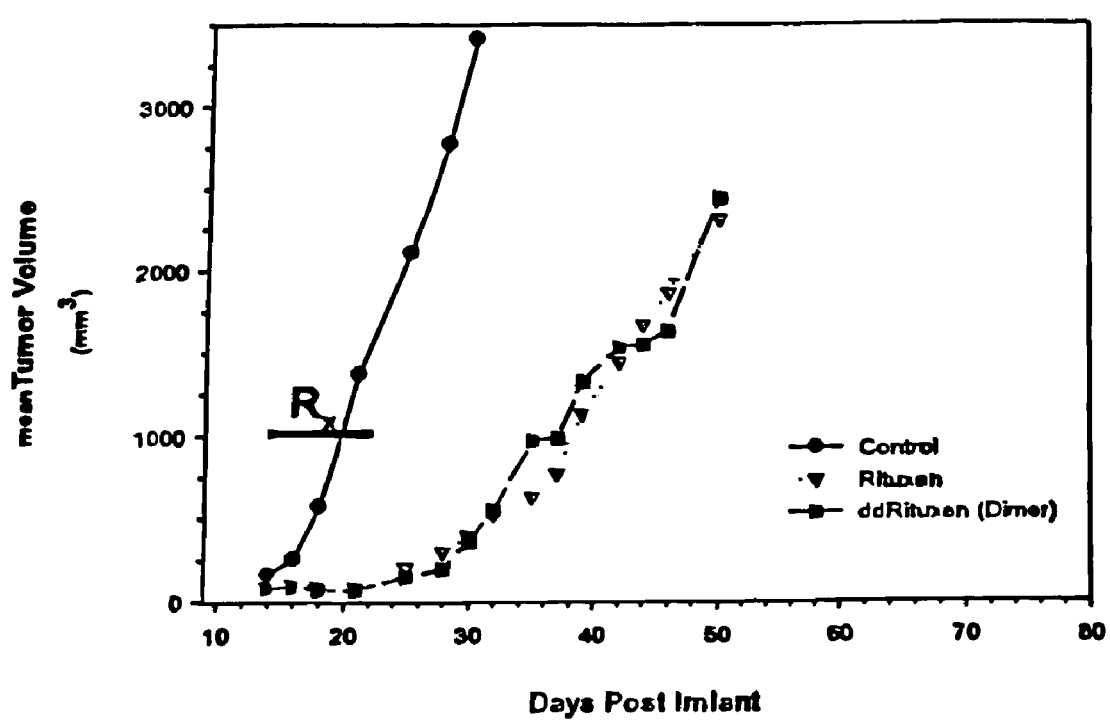
FIG. 13 graphically illustrates the antitumor activity of the dimeric variant of C2B8.$\Delta C_H2$ and Rituxan® in Daudi tumor xenografts.

FIG. 13 shows that the C2B8 homodimer is extremely active in murine animal models using a human B-lymphoma tumor xenograft, and demonstrated inhibition of tumor growth compared to the parent MAb, C2B8 (Rituxan). This clearly demonstrates that the unlabeled dimers of the present invention may be used efficaciously to retard or eliminate neoplastic growths.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

What is claimed is:

1. A kit useful for the treatment of a mammal suffering from or predisposed to a neoplastic disorder comprising at least one container containing substantially purified dimeric antibodies that bind specifically to TAG-72, each dimeric antibody comprising two antibodies that are non-covalently associated to form a tetravalent antibody dimer having four antigen-biding sites that bind specifically to TAG-72, wherein each of the antibodies in the dimer comprises two antibody heavy chain polypeptides having the heavy chain variable region amino acid sequence shown in FIG. 4A (SEQ ID NO: 7), and two antibody light chain polypeptides having the light chain variable region amino acid sequence shown in FIG. 5A (SEQ ID NO: 9), and has two antigen-binding sites that bind specifically to TAG-72;

wherein each of the four antibody heavy chain polypeptides in the dimeric antibody comprises a human gamma-1 constant region wherein a $C_H2$ domain is deleted from, and a $C_H3$ domain is fused directly to the hinge region;

wherein the dimeric tetravalent antibodies are purified to greater than 98% homogeneity;

and further comprising a label or an insert indicating that said dimeric antibody may be used to treat said neoplastic disorder.

2. Substantially purified dimeric antibodies that bind specifically to TAG-72, each dimeric antibody comprising two antibodies that are non-covalently associated to form a tetravalent antibody dimer having four antigen-binding sites that bind specifically to TAG-72, wherein each of the antibodies in the dimer comprises two antibody heavy chain polypeptides having the heavy chain variable region amino acid sequence shown in FIG. 4A (SEQ ID NO: 7), and two antibody light chain polypeptides having the light chain variable region amino acid sequence shown in FIG. 5A (SEQ ID NO: 9), and has two antigen-binding sites that bind specifically to TAG-72; and wherein each of the four antibody heavy chain polypeptides in the dimeric antibody comprises a human gamma-1 constant region wherein a $C_H2$ domain is deleted from, and a $C_H3$ domain is fused directly to the hinge region;

wherein the dimeric tetravalent antibodies are purified to greater than 98% homogeneity.

3. The substantially purified dimeric antibodies of claim 2, wherein said dimeric antibody is conjugated to a cytotoxic agent.

4. The substantially purified dimeric antibodies of claim 3, wherein said cytotoxic agent comprises a radioisotope.

5. The substantially purified dimeric antibodies of claim 4, wherein said radioisotope is selected from the group consisting of $^{90}Y$, $^{125}I$, $^{131}I$, $^{123}I$, $^{111}In$, $^{105}Rh$, $^{153}Sm$, $^{67}Cu$, $^{67}Ga$, $^{166}Ho$, 177Lu, $^{186}Re$ and $^{188}Re$.

6. The kit of claim 1, wherein said antibody dimer comprises four antibody heavy chain polypeptides having the heavy chain polypeptide amino acid sequence shown in FIG. 4A (SEQ ID NO: 7), and four antibody light chain polypeptides having the light chain polypeptide amino acid sequence shown in FIG. 5A (SEQ ID NO: 9).

7. The kit of claim 1 wherein said neoplastic disorder is colon cancer.

8. The substantially purified dimeric antibodies of claim 2, wherein said antibody dimer comprises four antibody heavy chain polypeptides having the heavy chain polypeptide amino acid sequence shown in FIG. 4A (SEQ ID NO: 7), and four antibody light chain polypeptides having the light chain polypeptide amino acid sequence shown in FIG. 5A (SEQ ID NO: 9).

9. The substantially purified dimeric antibodies of claim 3, wherein said cytotoxic agent is selected from the group consisting of cytostatic agents, alkylating agents, antimetabolites, anti-proliferative agents, tubulin binding agents, hormones and hormone antagonists, anthracycline drugs, vinca drugs, mitomycins, bleomycins, cytotoxic nucleosides, pteridine drugs, diynenes, podophyllotoxins, toxic enzymes, and radiosensitizing drugs.

10. The substantially purified dimeric antibodies of claim 9, wherein said cytotoxic agent is selected from the group consisting of mechlorethamine, triethylenephosphoramide, cyclophosphamide, ifosfamide, chlorambucil, busulfan, melphalan, triaziquone, nitrosourea compounds, adriamycin, carminomycin, daunorubicin (daunomycin), doxorubicin, aminopterin, methotrexate, methopterin, mithramycin, streptonigrin, dichloromethotrexate, mitomycin C, actinomycin-D, porfiromycin, 5-fluorouracil, floxuridine, ftorafur, 6-mercaptopurine, cytarabine, cytosine arabinoside, podophyllotoxin, etoposide, etoposide phosphate, melphalan, vinblastine, vincristine, leurosidine, vindesine, leurosine, taxol, taxane, cytochalasin B, gramicidin D, ethidium bromide, emetine, tenoposide, colchicin, dihydroxy anthracin dione, mitoxantrone, procaine, tetracaine, lidocaine, propranolol, puromycin, ricin subunit A, abrin, diptheria toxin, botulinum, cyanginosins, saxitoxin, shigatoxin, tetanus, tetrodotoxin, trichothecene, verrucologen, corticosteroids, progestins, estrogens, antiestrogens, androgens, aromatase inhibitors, calicheamicin, esperamicins, and dynemicins.

11. The substantially purified dimeric antibodies of claim 9, wherein said hormone or hormone antgonist is selected from the group consisting of prednisone, hydroxyprogesterone, medroprogesterone, diethylstilbestrol, tamoxifen, testosterone, and aminogluthetimide.

12. The substantially purified dimeric antibodies of claim 3, wherein said cytotoxic agent is a prodrug selected from the group consisting of phosphate-containing prodrugs, thiophosphate-containing prodrugs, sulfate containing prodrugs, peptide containing prodrugs, (-lactam-containing prodrugs, optionally substituted phenoxyacetamide-containing prodrugs, optionally substituted phenylacetamide-containing prodrugs, 5-fluorocytosinem, and 5-fluorouridine prodrugs that can be converted to the more active cytotoxic free drug.

13. A kit useful for the treatment of a mammal suffering from or predisposed to a neoplastic disorder comprising at least one container containing substantially purified dimeric antibodies that bind specifically to TAG-72, each dimeric antibody comprising two antibodies that are non-covalently associated to form a tetravalent antibody dimer having four antigen-binding sites that bind specifically to TAG-72, wherein each of the antibodies in the dimer comprises two antibody heavy chain polypeptides having the heavy chain polypeptide amino acid sequence shown in FIG. 4A (SEQ ID NO: 7) comprising a human gamma-1 constant region wherein the $C_H2$ domain is deleted and the $C_H3$ domain is fused directly to the hinge region, and two antibody light chain polypeptides having the light chain polypeptide amino acid sequence shown in FIG. 5A (SEQ ID NO: 9), and has two antigen-binding sites that bind specifically to TAG-72;

wherein the dimeric tetravalent antibodies are purified to greater than 98% homogeneity;

and further comprising a label or in insert indicating that said dimeric antibody may be used to treat said neoplastic disorder.

14. The kit of claim 13 wherein said neoplastic disorder is colon cancer.

15. Substantially purified dimeric antibodies that bind specifically to TAG-72, each dimeric antibody comprising two antibodies that are non-covalently associated to form a tetravalent antibody dimer having four antigen-binding sites that bind specifically to TAG-72, wherein each of the antibodies in the dimer comprises two antibody heavy chain polypeptides having the heavy chain polypeptide amino acid sequence shown in FIG. 4A (SEQ ID NO: 7) comprising a human gamma-1 constant region wherein the $C_H2$ domain is deleted and the $C_H3$ domain is fused directly to the hinge region, and two antibody light chain polypeptides having the light chain polypeptide amino acid sequence shown in FIG. 5A (SEQ ID NO: 9), and has two antigen-binding sites that bind specifically to TAG-72;

wherein the dimeric tetravalent antibodies are purified to greater than 98% homogeneity.

16. The substantially purified dimeric antibodies of claim 15, wherein said dimeric antibody is conjugated to a cytotoxic agent.

17. The substantially purified dimeric antibodies of claim 15, wherein said cytotoxic agent comprises a radioisotope.

18. The substantially purified dimeric antibodies of claim 15, wherein said radioisotope is selected from the group consisting of $^{90}Y$, $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$ and $^{188}Re$.

19. The substantially purified dimeric antibodies of claim 16, wherein said cytotoxic agent is selected from the group consisting of cytostatic agents, alkylating agents, antimetabolites, anti-proliferative agents, tubulin binding agents, hormones and hormone antagonists, anthracycline drugs, vinca drugs, mitomycins, bleomycins, cytotoxic nucleosides, pteridine drugs, diynenes, podophyllotoxins, toxic enzymes, and radiosensitizing drugs.

20. The substantially purified dimeric antibodies of claim 19, wherein said cytotoxic agent is selected from the group consisting of mechlorethamine, triethylenephosphoramide, cyclophosphamide, ifosfamide, chlorambucil, busulfan, melphalan, triaziquone, nitrosourea compounds, adriamycin, carminomycin, daunorubicin (daunomycin), doxorubicin, aminopterin, methotrexate, methopterin, mithramycin, streptonigrin, dichloromethotrexate, mitomycin C, atinomycin-D, porfiromycin, 5-fluorouracil, floxuridine, ftorafur, 6-mercaptopurine, cytarabine, cytosine arabinoside, podophyllotoxin, etoposide, etoposide phosphate, melphalan, vinblastine, vincristine, leurosidine, vindesine, leurosine, taxol, taxane, cytochalasin B, gramicidin D, ethidium bromide, emetine, tenoposide, colchicin, dihydroxy anthracin dione, mitoxantrone, procaine, tetracaine, lidocaine, propranolol, puromycin, ricin subunit A, abrin, diptheria toxin, botulinum, cyanginosins, saxitoxin, shigatoxin, tetanus, tetrodotoxin, trichothecene, verrucologen, corticosteroids, progestins, estrogens, antiestrogens, androgens, aromatase inhibitors, calichcamicin, esperamicins, and dynemicins.

21. The substantially purified dimeric antibodies of claim 19, wherein said hormone or hormone antagonist is selected from the group consisting of prednisone, hydroxyprogesterone, medroprogesterone, diethylstilbestrol, tamoxifen, testosterone, and aminogluthetimide.

22. The substantially purified dimeric antibodies of claim 16, wherein said cytotoxic agent is a prodrug selected from the group consisting of phosphate-containing prodrugs, thiophosphate-containing prodrugs, sulfate containing prodrugs, peptide containing prodrugs, (-lactam-containing prodrugs, optionally substituted phenoxyacetamide-containing prodrugs, optionally substituted phenylacetamide-containing prodrugs, 5-fluorocytosinem, and 5-fluorouridine prodrugs that can be converted to the more active cytotoxic free drug.

* * * * *

SEQUENCE LISTING

```
<160> NUMBER OF SEQ ID NOS: 17

<210> SEQ ID NO 1
<211> LENGTH: 470
<212> TYPE: PRT
<213> ORGANISM: Artificial Sequence
<220> FEATURE:
<223> OTHER INFORMATION: Description of Artificial Sequence: Synthetic
      C2B8 heavy chain amino acid sequence

<400> SEQUENCE: 1

Met Gly Trp Ser Leu Ile Leu Leu Phe Leu Val Ala Val Ala Thr Arg
 1               5                  10                  15

Val Leu Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Ala Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285
```

-continued

```
Val Ser His Glu Asp Pro Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 2
<211> LENGTH: 360
<212> TYPE: PRT
<213> ORGANISM: Artificial Sequence
<220> FEATURE:
<223> OTHER INFORMATION: Description of Artificial Sequence: Synthetic
      C2B8 domain deleted heavy chain amino acid sequence

<400> SEQUENCE: 2

Met Gly Trp Ser Leu Ile Leu Leu Phe Leu Val Ala Val Ala Thr Arg
  1               5                  10                  15

Val Leu Ser Gln Val Gln Leu Gln Gln Pro Gly Ala Glu Leu Val Lys
                 20                  25                  30

Pro Gly Ala Ser Val Lys Met Ser Cys Lys Ala Ser Gly Tyr Thr Phe
             35                  40                  45

Thr Ser Tyr Asn Met His Trp Val Lys Gln Thr Pro Gly Arg Gly Leu
         50                  55                  60

Glu Trp Ile Gly Ala Ile Tyr Pro Gly Asn Gly Asp Thr Ser Tyr Asn
 65                  70                  75                  80

Gln Lys Phe Lys Gly Lys Ala Thr Leu Thr Ala Asp Lys Ser Ser Ser
                 85                  90                  95

Thr Ala Tyr Met Gln Leu Ser Ser Leu Thr Ser Glu Asp Ser Ala Val
                100                 105                 110

Tyr Tyr Cys Ala Arg Ser Thr Tyr Tyr Gly Gly Asp Trp Tyr Phe Asn
            115                 120                 125

Val Trp Gly Ala Gly Thr Thr Val Thr Val Ser Ala Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175
```

-continued

```
Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
            210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
            290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
            355                 360

<210> SEQ ID NO 3
<211> LENGTH: 1412
<212> TYPE: DNA
<213> ORGANISM: Artificial Sequence
<220> FEATURE:
<223> OTHER INFORMATION: Description of Artificial Sequence: Synthetic
      C2B8 heavy chain nucleotide sequence

<400> SEQUENCE: 3
atgggttgga gcctcatctt gctcttcctt gtcgctgttg ctacgcgtgt cctgtcccag      60
gtacaactgc agcagcctgg ggctgagctg gtgaagcctg ggcctcagt gaagatgtcc      120 tgcaaggctt ctggctacac atttaccagt tacaatatgc actgggtaaa acagacacct     180
ggtcggggcc tggaatggat tggagctatt tatcccggaa atggtgatac ttcctacaat     240
cagaagttca aggcaaggc acattgact gcagacaaat cctccagcac agcctacatg      300
cagctcagca gcctgacatc tgaggactct gcggtctatt actgtgcaag atcgacttac    360
tacggcggtg actggtactt caatgtctgg ggcgcaggga ccacggtcac cgtctctgca    420
gctagcacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagaa agcagagccc    720
aaatcttgtg acaaaactca cacatgccca ccgtgcccag cacctgaact cctgggggga    780
ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cgcgggagga gcagtacaac    960
```

-continued

```
agcacgtacc gtgtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag gcagccccg agaaccacag gtgtacaccc tgcccccatc ccggatgagc    1140
tgaccaagaa ccaggtcagc ctgacctgcc tggtcaaagg cttctatccc agcgacatcg   1200
ccgtggagtg ggagagcaat gggcagccgg agaacaacta caagaccacg cctcccgtgc   1260
tggactccga cggctccttc ttcctctaca gcaagctcac cgtggacaag agcaggtggc   1320
agcaggggaa cgtcttctca tgctccgtga tgcatgaggc tctgcacaac cactacacgc   1380
agaagagcct ctccctgtct ccgggtaaat ga                                 1412
```

<210> SEQ ID NO 4
<211> LENGTH: 1083
<212> TYPE: DNA
<213> ORGANISM: Artificial Sequence
<220> FEATURE:
<223> OTHER INFORMATION: Description of Artificial Sequence: Synthetic
C2B8 domain deleted heavy chain nucleotide sequence

<400> SEQUENCE: 4

```
atgggttgga gcctcatctt gctcttcctt gtcgctgttg ctacgcgtgt cctgtcccag    60
gtacaactgc agcagcctgg ggctgagctg gtgaagcctg gggcctcagt gaagatgtcc   120
tgcaaggctt ctggctacac atttaccagt tacaatatgc actgggtaaa acagacacct   180
ggtcggggcc tggaatggat tggagctatt tatcccggaa atggtgatac ttcctacaat   240
cagaagttca aggcaaggc cacattgact gcagacaaat cctccagcac agcctacatg   300
cagctcagca gcctgacatc tgaggactct gcggtctatt actgtgcaag atcgacttac   360
tacggcggtg actggtactt caatgtctgg ggcgcaggga ccacggtcac cgtctctgca   420
gctagcacca agggcccatc ggtcttcccc ctggcaccct cctccaagag cacctctggg   480
ggcacagcgg ccctgggctg cctggtcaag gactacttcc ccgaaccggt gacggtgtcg   540
tggaactcag gcgccctgac cagcggcgtg cacaccttcc cggctgtcct acagtcctca   600
ggactctact ccctcagcag cgtggtgacc gtgccctcca gcagcttggg cacccagacc   660
tacatctgca acgtgaatca caagcccagc aacaccaagg tggacaagaa agttgagccc   720
aaatcttgtg acaaaactca cacatgccca ccgtgcccag gcagccccg agaaccacag   780 gtgtacaccc tgcccccatc ccggatgagc tgaccaaga accaggtcag cctgacctgc   840
ctggtcaaag gcttctatcc cagcgacatc gccgtggagt gggagagcaa tgggcagccg   900
gagaacaact acaagaccac gcctcccgtg ctggactccg acggctcctt cttcctctac   960
agcaagctca ccgtggacaa gagcaggtgg cagcagggga acgtcttctc atgctccgtg  1020
atgcatgagg ctctgcacaa ccactacacg cagaagagcc tctccctgtc tccgggtaaa  1080
tga                                                                1083
```

<210> SEQ ID NO 5
<211> LENGTH: 708
<212> TYPE: DNA
<213> ORGANISM: Artificial Sequence
<220> FEATURE:
<223> OTHER INFORMATION: Description of Artificial Sequence: Synthetic
C2B8 light chain nucleotide sequence

<400> SEQUENCE: 5

```
atggatttc aggtgcagat tatcagcttc ctgctaatca gtgcttcagt cataatgtcc     60
```

-continued

| | |
|---|---|
| agaggacaaa ttgttctctc ccagtctcca gcaatcctgt ctgcatctcc aggggagaag | 120 |
| gtcacaatga cttgcagggc cagctcaagt gtaagttaca tccactggtt ccagcagaag | 180 |
| ccaggatcct cccccaaacc ctggatttat gccacatcca acctggcttc tggagtccct | 240 |
| gttcgcttca gtggcagtgg gtctgggact tcttactctc tcacaatcag cagagtggag | 300 |
| gctgaagatg ctgccactta ttactgccag cagtggacta gtaacccacc cacgttcgga | 360 |
| ggggggacca agctggaaat caaacgtacg gtggctgcac catctgtctt catcttcccg | 420 |
| ccatctgatg agcagttgaa atctggaact gcctctgttg tgtgcctgct gaataacttc | 480 |
| tatcccagag aggccaaagt acagtggaag gtggataacg ccctccaatc gggtaactcc | 540 |
| caggagagtg tcacagagca ggacagcaag gacagcacct acagcctcag cagcaccctg | 600 |
| acgctgagca agcagactac gagaaacac aaagtctacg cctgcgaagt cacccatcag | 660 |
| ggcctgagct cgcccgtcac aaagagcttc aacaggggag agtgttga | 708 |

<210> SEQ ID NO 6
<211> LENGTH: 235
<212> TYPE: PRT
<213> ORGANISM: Artificial Sequence
<220> FEATURE:
<223> OTHER INFORMATION: Description of Artificial Sequence: Synthetic
    C2B8 light chain amino acid sequence

<400> SEQUENCE: 6

```
Met Asp Phe Gln Val Gln Ile Ile Ser Phe Leu Leu Ile Ser Ala Ser
  1               5                  10                  15

Val Ile Met Ser Arg Gly Gln Ile Val Leu Ser Gln Ser Pro Ala Ile
             20                  25                  30

Leu Ser Ala Ser Pro Gly Glu Lys Val Thr Met Thr Cys Arg Ala Ser
         35                  40                  45

Ser Ser Val Ser Tyr Ile His Trp Phe Gln Gln Lys Pro Gly Ser Ser
     50                  55                  60

Pro Lys Pro Trp Ile Tyr Ala Thr Ser Asn Leu Ala Ser Gly Val Pro
 65                  70                  75                  80

Val Arg Phe Ser Gly Ser Gly Ser Gly Thr Ser Tyr Ser Leu Thr Ile
                 85                  90                  95

Ser Arg Val Glu Ala Glu Asp Ala Ala Thr Tyr Tyr Cys Gln Gln Trp
            100                 105                 110

Thr Ser Asn Pro Pro Thr Phe Gly Gly Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 7
<211> LENGTH: 354
<212> TYPE: PRT
<213> ORGANISM: Artificial Sequence
<220> FEATURE:
<223> OTHER INFORMATION: Description of Artificial Sequence: Synthetic HuCC49 domain deleted heavy chain amino acid sequence

<400> SEQUENCE: 7

```
Met Gly Trp Ser Leu Ile Leu Leu Phe Leu Val Ala Val Ala Thr Arg
 1               5                  10                  15

Val Leu Ser Gln Val Gln Leu Val Gln Ser Gly Ala Glu Val Val Lys
            20                  25                  30

Pro Gly Ala Ser Val Lys Ile Ser Cys Lys Ala Ser Gly Tyr Thr Phe
        35                  40                  45

Thr Asp His Ala Ile His Trp Val Lys Gln Asn Pro Gly Gln Arg Leu
    50                  55                  60

Glu Trp Ile Gly Tyr Phe Ser Pro Gly Asn Asp Asp Phe Lys Tyr Asn
65                  70                  75                  80

Glu Arg Phe Lys Gly Lys Ala Thr Leu Thr Ala Asp Thr Ser Ala Ser
                85                  90                  95

Thr Ala Tyr Val Glu Leu Ser Ser Leu Arg Ser Glu Asp Thr Ala Val
            100                 105                 110

Tyr Phe Cys Thr Arg Ser Leu Asn Met Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Gly Gln Pro Arg Glu Pro Gln Val Tyr
                245                 250                 255

Thr Leu Pro Pro Ser Arg Asp Glu Leu Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys
```

-continued

<210> SEQ ID NO 8
<211> LENGTH: 1065
<212> TYPE: DNA
<213> ORGANISM: Artificial Sequence
<220> FEATURE:
<223> OTHER INFORMATION: Description of Artificial Sequence: Synthetic
      HuCC49 domain deleted heavy chain nucleotide sequence

<400> SEQUENCE: 8

```
atgggttgga gcctcatctt gctcttcctt gtcgctgttg ctacgcgtgt cctgtcccag      60
gtccagctgg tgcagtccgg cgctgaggtg gtgaaacctg gggcttccgt gaagatttcc     120
tgcaaggcaa gcggctacac cttcactgat cacgcaatcc actgggtgaa acagaatcct    180
ggacagcgcc tggagtggat tggatatttc tctcccggaa cgatgatttt aagtacaat      240 gagaggttca aggcaaggc cacactgact gcagacacat ctgccagcac tgcctacgtg      300
gagctctcca gcctgagatc cgaggatact gcagtgtact tctgcacaag atccctgaat    360
atggcctact ggggacaggg aaccctggtc accgtctcca gcgctagcac caagggccca    420
tcggtcttcc ccctggcacc ctcctccaag agcacctctg ggggcacagc ggccctgggc    480
tgcctggtca aggactactt ccccgaaccg gtgacggtgt cgtggaactc aggcgccctg    540
accagcggcg tgcacacctt cccggctgtc ctacagtcct caggactcta ctccctcagc    600
agcgtggtga ccgtgccctc cagcagcttg ggcacccaga cctacatctg caacgtgaat    660
cacaagccca gcaacaccaa ggtggacaag aaagttgagc ccaaatcttg tgacaaaact    720
cacacatgcc caccgtgccc agggcagccc cgagaaccac aggtgtacac cctgccccca    780
tcccgggatg agctgaccaa gaaccaggtc agcctgacct gcctggtcaa aggcttctat    840
cccagcgaca tcgccgtgga gtgggagagc aatgggcagc cggagaacaa ctacaagacc    900
acgcctcccg tgctggactc cgacggctcc ttcttcctct acagcaagct caccgtggac    960
aagagcaggt ggcagcaggg gaacgtcttc tcatgctccg tgatgcatga ggctctgcac    1020
aaccactaca cgcagaagag cctctccctg tctccgggta aatga                    1065
```

<210> SEQ ID NO 9
<211> LENGTH: 240
<212> TYPE: PRT
<213> ORGANISM: Artificial Sequence
<220> FEATURE:
<223> OTHER INFORMATION: Description of Artificial Sequence: Synthetic
      HuCC49 light chain amino acid sequence

<400> SEQUENCE: 9

```
Met Asp Ser Gln Ala Gln Val Leu Met Leu Leu Leu Leu Trp Val Ser
  1               5                  10                  15

Gly Thr Cys Gly Asp Ile Val Met Ser Gln Ser Pro Asp Ser Leu Ala
                 20                  25                  30

Val Ser Leu Gly Glu Arg Val Thr Leu Asn Cys Lys Ser Ser Gln Ser
             35                  40                  45

Leu Leu Tyr Ser Gly Asn Gln Lys Asn Tyr Leu Ala Trp Tyr Gln Gln
         50                  55                  60

Lys Pro Gly Gln Ser Pro Lys Leu Leu Ile Tyr Trp Ala Ser Ala Arg
 65                  70                  75                  80

Glu Ser Gly Val Pro Asp Arg Phe Ser Gly Ser Gly Ser Gly Thr Asp
                 85                  90                  95

Phe Thr Leu Thr Ile Ser Ser Val Gln Ala Glu Asp Val Ala Val Tyr
                100                 105                 110

Tyr Cys Gln Gln Tyr Tyr Ser Tyr Pro Leu Thr Phe Gly Ala Gly Thr
```

-continued

```
                 115                 120                     125
Lys Leu Glu Leu Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 10
<211> LENGTH: 723
<212> TYPE: DNA
<213> ORGANISM: Artificial Sequence
<220> FEATURE:
<223> OTHER INFORMATION: Description of Artificial Sequence: Synthetic
      HuCC49 light chain nucleotide sequence

<400> SEQUENCE: 10
atggatagcc aggcccaggt gctcatgctc ctgctgctgt gggtgagcgg cacatgcggc      60
gacatcgtga tgagccagtc tccagactcc ctggccgtgt ccctgggcga gagggtgact     120
ctgaattgca gtccagcca gtccctgctc tatagcggaa atcagaagaa ctatctcgcc      180
tggtatcagc agaaaccagg gcagagccct aaactgctga tttactgggc atccgctagg     240
gaatccggcg tgcctgatcg cttcagcggc agcggatctg ggacagactt cactctgaca     300
atcagcagcg tgcaggcaga agacgtggca gtctattatt gtcagcagta ttatagctat     360
cccctcacat cggcgctgg caccaagctg gaactgaaaa cgtacggtgg ctgcaccatct     420 gtcttcatct tcccgccatc tgatgagcag ttgaaatctg gaactgcctc tgttgtgtgc     480
ctgctgaata acttctatcc cagagaggcc aaagtacagt ggaaggtgga taacgccctc     540
caatcgggta actcccagga gagtgtcaca gagcaggaca gcaaggacag cacctacagc     600
ctcagcagca ccctgacgct gagcaaagca gactacgaga aacacaaagt ctacgcctgc     660
gaagtcaccc atcagggcct gagctcgccc gtcacaaaga gcttcaacag gggagagtgt     720
tga                                                                   723

<210> SEQ ID NO 11
<211> LENGTH: 468
<212> TYPE: PRT
<213> ORGANISM: Artificial Sequence
<220> FEATURE:
<223> OTHER INFORMATION: Description of Artificial Sequence: Synthetic
      C5E10 heavy chain amino acid sequence

<400> SEQUENCE: 11

Met Ala Val Leu Ala Leu Leu Phe Cys Leu Val Thr Phe Pro Ser Cys
1               5                   10                  15

Ile Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45
```

```
Thr Asp Tyr Gly Val Asn Trp Val Arg Gln Pro Pro Gly Lys Gly Leu
 50                  55                  60
Glu Trp Leu Gly Met Ile Trp Asp Asn Gly Arg Thr Asp Tyr Asn Ser
 65                  70                  75                  80
Ala Leu Lys Ser Arg Leu Ser Ile Asn Lys Asp Asn Ser Lys Ser Gln
                 85                  90                  95
Val Phe Leu Lys Met Thr Ser Leu Gln Thr Asp Asp Thr Ala Arg Tyr
            100                 105                 110
Tyr Cys Ala Arg Cys Tyr Tyr Gly Ser Ser Pro Tyr Phe Asp Tyr Trp
            115                 120                 125
Gly Gln Gly Thr Thr Leu Thr Val Ser Ser Ala Ser Thr Lys Gly Pro
            130                 135                 140
Ser Val Phe Pro Leu Ala Pro Ser Ser Lys Ser Thr Ser Gly Gly Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
                180                 185                 190
Ala Val Leu Gln Ser Ser Gly Leu Tyr Ser Leu Ser Ser Val Val Thr
            195                 200                 205
Val Pro Ser Ser Ser Leu Gly Thr Gln Thr Tyr Ile Cys Asn Val Asn
            210                 215                 220
His Lys Pro Ser Asn Thr Lys Val Asp Lys Lys Val Glu Pro Lys Ser
225                 230                 235                 240
Cys Asp Lys Thr His Thr Cys Pro Pro Cys Pro Ala Pro Glu Leu Leu
                245                 250                 255
Gly Gly Pro Ser Val Phe Leu Phe Pro Pro Lys Pro Lys Asp Thr Leu
                260                 265                 270
Met Ile Ser Arg Thr Pro Glu Val Thr Cys Val Val Val Asp Val Ser
            275                 280                 285
His Glu Asp Pro Glu Val Lys Phe Asn Trp Tyr Val Asp Gly Val Glu
290                 295                 300
Val His Asn Ala Lys Thr Lys Pro Arg Glu Glu Gln Tyr Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Ala Leu Pro Ala Pro
            340                 345                 350
Ile Glu Lys Thr Ile Ser Lys Ala Lys Gly Gln Pro Arg Glu Pro Gln
            355                 360                 365
Val Tyr Thr Leu Pro Pro Ser Arg Asp Glu Leu Thr Lys Asn Gln Val
            370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Lys Leu Thr
            420                 425                 430
Val Asp Lys Ser Arg Trp Gln Gln Gly Asn Val Phe Ser Cys Ser Val
            435                 440                 445
Met His Glu Ala Leu His Asn His Tyr Thr Gln Lys Ser Leu Ser Leu
450                 455                 460
```

Ser Pro Gly Lys
465

<210> SEQ ID NO 12
<211> LENGTH: 358
<212> TYPE: PRT
<213> ORGANISM: Artificial Sequence
<220> FEATURE:
<223> OTHER INFORMATION: Description of Artificial Sequence: Synthetic C5E10 domain deleted heavy chain amino acid sequence

<400> SEQUENCE: 12

```
Met Ala Val Leu Ala Leu Leu Phe Cys Leu Val Thr Phe Pro Ser Cys
 1               5                  10                  15

Ile Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Asp Tyr Gly Val Asn Trp Val Arg Gln Pro Pro Gly Lys Gly Leu
    50                  55                  60

Glu Trp Leu Gly Met Ile Trp Asp Asn Gly Arg Thr Asp Tyr Asn Ser
65                  70                  75                  80

Ala Leu Lys Ser Arg Leu Ser Ile Asn Lys Asp Asn Ser Lys Ser Gln
                85                  90                  95

Val Phe Leu Lys Met Thr Ser Leu Gln Thr Asp Asp Thr Ala Arg Tyr
            100                 105                 110

Tyr Cys Ala Arg Cys Tyr Tyr Gly Ser Ser Pro Tyr Phe Asp Tyr Trp
        115                 120                 125

Gly Gln Gly Thr Thr Leu Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350
```

Ser Leu Ser Pro Gly Lys
     355

<210> SEQ ID NO 13
<211> LENGTH: 1407
<212> TYPE: DNA
<213> ORGANISM: Artificial Sequence
<220> FEATURE:
<223> OTHER INFORMATION: Description of Artificial Sequence: Synthetic
      C5E10 heavy chain nucleotide sequence

<400> SEQUENCE: 13

| | |
|---|---|
| atggctgtct tagcgctact cttctgcctg gtaacattcc caagctgtat cctttcccag | 60 |
| gtgcagctga aggagtcagg acctggcctg gtggcgccct cacagagcct gtccatcaca | 120 |
| tgcaccgtct cagggttctc attaaccgac tatggtgtaa actgggttcg ccagcctcca | 180 |
| ggaaagggtc tggagtggct tggaatgata tgggataatg aagaacaga ctataattca | 240 |
| gctctcaaat ccagactgag catcaacaag acaactcca agagccaagt tttcttaaaa | 300 |
| atgaccagtc tgcaaactga tgacacagcc aggtactact gtgccagatg ctattacggt | 360 |
| agtagccctt actttgacta ctggggccaa ggcaccactc tcaccgtctc ctcagctagc | 420 |
| accaagggcc catcggtctt cccccctggca ccctcctcca agagcacctc tgggggcaca | 480 |
| gcggccctgg gctgcctggt caaggactac ttccccgaac cggtgacggt gtcgtggaac | 540 |
| tcaggcgccc tgaccagcgg cgtgcacacc ttcccggctg tcctacagtc ctcaggactc | 600 |
| tactccctca gcagcgtggt gaccgtgccc tccagcagct tgggcaccca gacctacatc | 660 |
| tgcaacgtga atcacaagcc cagcaacacc aaggtggaca gaaagttga gcccaaatct | 720 |
| tgtgacaaaa ctcacacatg cccaccgtgc ccagcacctg aactcctggg gggaccgtca | 780 |
| gtcttcctct tccccccaaa acccaaggac accctcatga tctcccggac ccctgaggtc | 840 |
| acatgcgtgg tggtggacgt gagccacgaa gaccctgagg tcaagttcaa ctggtacgtg | 900 |
| gacggcgtgg aggtgcataa tgccaagaca aagccgcggg aggagcagta caacagcacg | 960 |
| taccgtgtgg tcagcgtcct caccgtcctg caccaggact ggctgaatgg caaggagtac | 1020 |
| aagtgcaagg tctccaacaa agccctccca gcccccatcg agaaaaccat ctccaaagcc | 1080 |
| aaagggcagc cccgagaacc acaggtgtac accctgcccc catcccggga tgagctgacc | 1140 |
| aagaaccagg tcagcctgac ctgcctggtc aaaggcttct atcccagcga catcgccgtg | 1200 |
| gagtgggaga gcaatgggca gccggagaac aactacaaga ccacgcctcc cgtgctggac | 1260 |
| tccgacggct ccttcttcct ctacagcaag ctcaccgtgg acaagagcag gtggcagcag | 1320 |
| gggaacgtct tctcatgctc cgtgatgcat gaggctctgc acaaccacta cacgcagaag | 1380 |
| agcctctccc tgtctccggg taaatga | 1407 |

<210> SEQ ID NO 14
<211> LENGTH: 1077
<212> TYPE: DNA
<213> ORGANISM: Artificial Sequence
<220> FEATURE:
<223> OTHER INFORMATION: Description of Artificial Sequence: Synthetic
      C5E10 domain deleted heavy chain nucleotide sequence

<400> SEQUENCE: 14

| | |
|---|---|
| atggctgtct tagcgctact cttctgcctg gtaacattcc caagctgtat cctttcccag | 60 |
| gtgcagctga aggagtcagg acctggcctg gtggcgccct cacagagcct gtccatcaca | 120 |
| tgcaccgtct cagggttctc attaaccgac tatggtgtaa actgggttcg ccagcctcca | 180 |

```
ggaaagggtc tggagtggct tggaatgata tgggataatg aagaacaga ctataattca    240 gctctcaaat ccagactgag catcaacaag acaactcca agagccaagt tttcttaaaa    300
atgaccagtc tgcaaactga tgacacagcc aggtactact gtgccagatg ctattacggt    360
agtagccctt actttgacta ctggggccaa ggcaccactc tcaccgtctc ctcagctagc    420
accaagggcc catcggtctt ccccctggca ccctcctcca agagcacctc tgggggcaca    480
gcggccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct gggcaccca gacctacatc    660 tgcaacgtga atcacaagcc cagcaacacc aaggtggaca gaaagttga gcccaaatct    720 tgtgacaaaa ctcacacatg cccaccgtgc ccagggcagc ccgagaacc acaggtgtac    780 accctgcccc catcccggga tgagctgacc aagaaccagg tcagcctgac ctgcctggtc    840
aaaggcttct atcccagcga catcgccgtg gagtgggaga gcaatgggca gccggagaac    900
aactacaaga ccacgcctcc cgtgctggac tccgacggct ccttcttcct ctacagcaag    960
ctcaccgtgg acaagagcag gtggcagcag gggaacgtct tctcatgctc cgtgatgcat   1020
gaggctctgc acaaccacta cacgcagaag agcctctccc tgtctccggg taaatga      1077

<210> SEQ ID NO 15
<211> LENGTH: 717
<212> TYPE: DNA
<213> ORGANISM: Artificial Sequence
<220> FEATURE:
<223> OTHER INFORMATION: Description of Artificial Sequence: Synthetic
      C5E10 light chain nucleotide sequence

<400> SEQUENCE: 15
atgggcatca agatggagtc acattctctg gtctttgtat acatgttgct gtggttgtct     60
ggtgttgaag agacattgt gatgatccag tctcacaaat tcatgtccac atcagtagga    120
gacagggtca gcatcacctg caaggccagt caggatgtgg gtactgctgt cgcctggtat    180
caacagaaac caggacaatc tcctaaacta ctgatttact ggtcatccac ccggcacact    240
ggagtccctg atcgcttcac aggcagtgga tctgggacag atttcactct caccattagc    300
aatgtgcagt ctgaagactt ggcagattat ttctgtcagt atatagcag ctatcctctc    360 acgttcggag gggggaccaa gctggaaatc aaacgtacgg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca agtctacgc ctgcgaagtc    660 acccatcagg gcctgagctc gcccgtcaca aagagcttca caggggaga gtgttga      717

<210> SEQ ID NO 16
<211> LENGTH: 238
<212> TYPE: PRT
<213> ORGANISM: Artificial Sequence
<220> FEATURE:
<223> OTHER INFORMATION: Description of Artificial Sequence: Synthetic
      C5E10 light chain amino acid sequence

<400> SEQUENCE: 16

Met Gly Ile Lys Met Glu Ser His Ser Leu Val Phe Val Tyr Met Leu
 1               5                  10                  15
```

-continued

```
Leu Trp Leu Ser Gly Val Glu Gly Asp Ile Val Met Ile Gln Ser His
            20                  25                  30

Lys Phe Met Ser Thr Ser Val Gly Asp Arg Val Ser Ile Thr Cys Lys
        35                  40                  45

Ala Ser Gln Asp Val Gly Thr Ala Val Ala Trp Tyr Gln Gln Lys Pro
    50                  55                  60

Gly Gln Ser Pro Lys Leu Leu Ile Tyr Trp Ser Ser Thr Arg His Thr
65                  70                  75                  80

Gly Val Pro Asp Arg Phe Thr Gly Ser Gly Ser Gly Thr Asp Phe Thr
                85                  90                  95

Leu Thr Ile Ser Asn Val Gln Ser Glu Asp Leu Ala Asp Tyr Phe Cys
            100                 105                 110

Gln Leu Tyr Ser Ser Tyr Pro Leu Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      short amino acid spacer

<400> SEQUENCE: 17

Gly Gly Ser Ser Gly Gly Gly Gly Ser Gly
1               5                   10
```